US011045467B2

(12) United States Patent
Huang

(10) Patent No.: US 11,045,467 B2
(45) Date of Patent: *Jun. 29, 2021

(54) METHOD OF TREATING CANCER ASSOCIATED WITH A RAS MUTATION

(71) Applicant: BeyondSpring Pharmaceuticals, Inc., New York, NY (US)

(72) Inventor: Lan Huang, Bronx, NY (US)

(73) Assignee: BeyondSpring Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/889,251

(22) Filed: Jun. 1, 2020

(65) Prior Publication Data

US 2020/0289503 A1    Sep. 17, 2020

Related U.S. Application Data

(63) Continuation of application No. 16/290,765, filed on Mar. 1, 2019, now Pat. No. 10,668,063, which is a continuation of application No. 15/555,963, filed as application No. PCT/US2016/020390 on Mar. 2, 2016, now Pat. No. 10,238,650.

(60) Provisional application No. 62/129,654, filed on Mar. 6, 2015, provisional application No. 62/249,788, filed on Nov. 2, 2015.

(51) Int. Cl.
*A61K 31/496* (2006.01)
*A61K 45/06* (2006.01)
*A61P 35/00* (2006.01)
*A61K 31/337* (2006.01)
*A61K 31/4745* (2006.01)

(52) U.S. Cl.
CPC .......... *A61K 31/496* (2013.01); *A61K 31/337* (2013.01); *A61K 31/4745* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 4,535,183 A | 8/1985 | Kneen |
| 5,607,934 A | 3/1997 | Tone et al. |
| 5,733,888 A | 3/1998 | Carver et al. |
| 5,852,018 A | 12/1998 | Bryans et al. |
| 5,872,151 A | 2/1999 | Rhodes |
| 5,874,443 A | 2/1999 | Kiely et al. |
| 5,886,210 A | 3/1999 | Rayle et al. |
| 5,891,877 A | 4/1999 | Brocchini et al. |
| 5,922,683 A | 7/1999 | Or et al. |
| 5,939,098 A | 8/1999 | Reidenberg et al. |
| 5,958,980 A | 9/1999 | Rhodes |
| 6,069,146 A | 5/2000 | Fenical et al. |
| 6,096,786 A | 8/2000 | Rhodes |
| 6,350,759 B1 | 2/2002 | Casara et al. |
| 6,358,957 B1 | 3/2002 | Fukumoto et al. |
| 6,500,825 B2 | 12/2002 | Lan et al. |
| 6,506,787 B2 | 1/2003 | Fujishita et al. |
| 6,509,331 B1 | 1/2003 | Audia et al. |
| 6,583,143 B2 | 6/2003 | Haddach |
| 6,713,480 B2 | 3/2004 | Fukumoto et al. |
| 6,808,710 B1 | 10/2004 | Wood et al. |
| 6,972,289 B1 | 12/2005 | Kanzaki et al. |
| 7,026,322 B2 | 4/2006 | Hayashi et al. |
| 7,064,201 B2 | 6/2006 | Hayashi et al. |
| 7,488,802 B2 | 2/2009 | Collins et al. |
| 7,629,380 B2 | 12/2009 | McMorris et al. |
| 7,635,757 B2 | 12/2009 | Freeman et al. |
| 7,674,903 B2 | 3/2010 | Hayashi et al. |
| 7,700,615 B2 | 4/2010 | Edwards et al. |
| 7,919,497 B2 | 4/2011 | Palladino et al. |
| 7,935,704 B2 | 5/2011 | Palladino et al. |
| 7,943,743 B2 | 5/2011 | Korman et al. |
| 7,956,058 B2 | 6/2011 | Hayashi et al. |
| 8,008,449 B2 | 8/2011 | Korman et al. |
| 8,129,527 B2 | 3/2012 | Palladino et al. |
| 8,168,757 B2 | 5/2012 | Finnefrock et al. |
| 8,217,149 B2 | 7/2012 | Irving et al. |
| 8,247,552 B2 | 8/2012 | Palladino et al. |
| 9,358,289 B2 | 6/2016 | Korman et al. |
| 9,394,368 B2 | 7/2016 | Brogdon et al. |
| 10,076,518 B2 | 9/2018 | Huang |
| 10,155,748 B2 | 12/2018 | Huang et al. |
| 10,238,650 B2 * | 3/2019 | Huang .................. A61K 45/06 |
| 10,357,491 B2 | 7/2019 | Huang |

(Continued)

FOREIGN PATENT DOCUMENTS

EA    016817 B1    7/2012
EP    0 054 924    6/1982

(Continued)

OTHER PUBLICATIONS

Abels, Christoph, Targeting of the Vascular System of Solid Tumours by Photodynamic Therapy (PDT), Photochem Photobiol Sci., (Mar. 2004) 3: 765-771.
Abstracts of The 1999 Joint Chubu and Kansai Branch Conference and Symposia of Japan Society for Bioscience, Biotechnology, and Agrochemistry, (1999) p. 48.
Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.
Aggarwal et al., Antiangiogenic agents in the management of non-small cell lung cancer: Where do we stand now and where are we headed? Cancer Biology & Therapy (2012), 13(5), 247-263.

(Continued)

*Primary Examiner* — Brian J Davis
(74) *Attorney, Agent, or Firm* — Knobbe, Martens, Olson & Bear, LLP

(57) ABSTRACT

Disclosed herein are methods of treating a cancer characterized by expressing a mutant form of a RAS protein. Some embodiments relate to treatment of cancer by administering Plinabulin to a subject in need thereof.

20 Claims, 6 Drawing Sheets

(56) References Cited

U.S. PATENT DOCUMENTS

| | | | |
|---|---|---|---|
| 10,550,104 | B2 | 2/2020 | Huang et al. |
| 10,596,169 | B2 | 3/2020 | Huang |
| 10,668,063 | B2 * | 6/2020 | Huang .................. A61K 31/496 |
| 2002/0028819 | A1 | 3/2002 | Teng et al. |
| 2002/0143021 | A1 | 10/2002 | Fukumoto et al. |
| 2004/0102454 | A1 | 5/2004 | Hayashi et al. |
| 2006/0079534 | A1 | 4/2006 | Kanzaki et al. |
| 2006/0167010 | A1 | 7/2006 | Hayashi et al. |
| 2006/0223822 | A1 | 10/2006 | Hayashi et al. |
| 2007/0293453 | A1 | 12/2007 | Fisher et al. |
| 2008/0199485 | A1 | 8/2008 | Kundig et al. |
| 2008/0255035 | A1 | 10/2008 | Trieu et al. |
| 2009/0170837 | A1 | 7/2009 | Gourdeau et al. |
| 2009/0317368 | A1 | 12/2009 | Chen |
| 2012/0041070 | A1 | 2/2012 | Shengfan et al. |
| 2012/0277251 | A1 | 11/2012 | Palladino et al. |
| 2013/0303481 | A1 | 11/2013 | Marcus |
| 2014/0322275 | A1 | 10/2014 | Brogdon et al. |
| 2015/0202291 | A1 | 7/2015 | Bosch et al. |
| 2015/0291549 | A1 | 10/2015 | Chupak et al. |
| 2016/0243153 | A1 | 8/2016 | Sundaram et al. |
| 2017/0226221 | A1 | 8/2017 | Madiyalakan et al. |
| 2018/0028531 | A1 | 2/2018 | Huang et al. |
| 2019/0175587 | A1 | 6/2019 | Huang et al. |
| 2019/0380983 | A1 | 12/2019 | Mohanlal |
| 2020/0038395 | A1 | 2/2020 | Mohanlal |
| 2020/0129504 | A1 | 4/2020 | Mohanlal et al. |

FOREIGN PATENT DOCUMENTS

| | | |
|---|---|---|
| EP | 0 655 060 | 1/1998 |
| GB | 2143823 | 2/1985 |
| JP | 05-9164 | 1/1993 |
| JP | 05-255106 | 10/1993 |
| JP | 10-130266 | 5/1998 |
| JP | 2002-507612 A | 3/2002 |
| RU | 2011 148 945 A | 4/2010 |
| WO | WO 87/05297 | 9/1987 |
| WO | WO 94/07479 | 4/1994 |
| WO | WO 95/06077 | 3/1995 |
| WO | WO 95/21832 | 8/1995 |
| WO | WO 96/20190 | 7/1996 |
| WO | WO 99/38844 | 8/1999 |
| WO | WO 99/048889 | 9/1999 |
| WO | WO 01/053290 | 7/2001 |
| WO | WO 01/070663 | 9/2001 |
| WO | WO 04/054498 | 7/2004 |
| WO | WO 04/093831 | 11/2004 |
| WO | WO 05/077940 | 8/2005 |
| WO | WO 06/121168 | 11/2006 |
| WO | WO 08/128169 | 10/2008 |
| WO | WO 09/089260 | 7/2009 |
| WO | WO 10/001169 | 1/2010 |
| WO | WO 11/034954 | 3/2011 |
| WO | WO 11/050344 | 5/2011 |
| WO | WO 11/066389 | 6/2011 |
| WO | WO 11/079507 | 7/2011 |
| WO | WO 11/109625 | 9/2011 |
| WO | WO 11/146382 | 11/2011 |
| WO | WO 11/151423 | 12/2011 |
| WO | WO 12/014549 | 2/2012 |
| WO | WO 12/035436 | 3/2012 |
| WO | WO 12/074904 | 6/2012 |
| WO | WO 12/145493 | 10/2012 |
| WO | WO 13/078537 | 6/2013 |
| WO | WO 13/090552 | 6/2013 |
| WO | WO 13/177633 | 12/2013 |
| WO | WO 14/066834 | 5/2014 |
| WO | WO 14/130657 | 8/2014 |
| WO | WO 14/160183 | 10/2014 |
| WO | WO 14/195852 | 12/2014 |
| WO | WO 15/069790 | 5/2015 |
| WO | WO 15/160641 | 10/2015 |
| WO | WO 17/062505 | 4/2017 |
| WO | WO 18/129381 | 7/2018 |

OTHER PUBLICATIONS

Ahmed et al. "A new rapid and simple non-radioactive assay to monitor and determine the proliferation of lymphocytes: an alternative to [$^3$H]thymidine incorporation assay." J. Immunol. Methods. 170, 211-224 (1994).

Akerlund et al., "Diketopiperazine-Based Polymers from Common Amino Acids," Journal of Applied Polymer Science, (2000) 78 (12), 2213-2218.

Algaier et al. "The effects of dimethyl sulfoxide on the kinetics of tubulin assembly." Biochim. Biophys. Acta. 954, 235-43 (1988).

Ali et al. "Toxicity of echinulin from Aspergillus chevalieri in rabbits." Toxicology Letters. (1989) 48: 235-41.

Asahina, T., "Spectrochemical Study of Amino-acid Anhydrides," Bulletin of the Chemical Society of Japan, (1930) 5, 354-365.

Augustin, M. "Die Umsetzung des 2,5-Diketopiperazins mit Aldehyden und Nitrosoverbindungen" Journal für Praktische Chemie, (1966) 32(4), 158-166.

Aviel-Ronen et al., "K-ras Mutations in Non-Small-Cell Lung Carcinoma: A Review," *Clinical Lung Cancer* (Jul. 2006) vol. 8, No. 1, pp. 30-38.

Bankowska et al., Derivatives of 1,2,3-triazole. Potential drugs?, Wiadomosci Chemiczne (2012), 66(11-12), 993-1022.

Beavis et al., "Dual PD-1 and CTLA-4 Checkpoint Blockade Promotes Antitumor Immune Responses through CD4$^+$Foxp$^3$-Cell-Mediated Modulation of CD103$^+$ Dendritic Cells," Cancer Immunol Res (Sep. 2018) 6(9):1069-1081.

Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.

Bertelsen et al., "Vascular effects of plinabulin (NPI-2358) and the influence on tumour response when given alone or combined with radiation," International Journal of Radiation Biology (2011),87(11), 1126-1134.

Bertino J., et al., "Principles of Cancer Therapy." Cecil Textbook of Medicine. Eds. Lee Goldman, et al. 21nd ed., (2000), Chapter 198, pp. 1060-1074.

Blayney et al., "Plinabulin, a Novel Small Molecule That Ameliorates Chemotherapy-Induced Neutropenia, Is Administered on the Same Day of Chemotherapy and Has Anticancer Efficacy", Meeting Info.: 58th Annual Meeting and Exposition of the American Society-of-Hematology (ASH), Blood (2016) 128(22): 2508.

Bond et al. "The Synthesis of Viridamine, a Penicillium Viridicatum Mycotoxin." Synthetic Commun. 19 (13&14), 2551-2566 (1989).

Borisy, G.G. "A Rapid Method for Quantitative Determination of Microtubule Protein using DEAE-Cellulose Filters." Anal. Biochem. 50, 373-385 (1972).

Brahmer et al., "Safety and Activity of Anti-PD-L1 Antibody in Patients with Advanced Cancer," N Engl J Med (2012) 366:2455-2465.

Burtles, Sally, "Transition from Preclinical to first-in-man Phase", Expert Scientific Group on Phase One Clinical Trials Final Report, Presentation Jun. 19, 2006, pp. 35-38.

Cai, Small molecule vascular disrupting agents: potential new drugs for cancer treatment, a 2009 update, Frontiers in Anti-Cancer Drug Discovery (2010), 1, 380-427.

Cai, Sui X., "Small Molecule Vascular Disrupting Agents: Potential New Drugs for Cancer Treatment", Recent Pat Anticancer Drug Discov. (2007) 2(1): 79-101.

Callahan et al., "At the Bedside: CTLA-4- and PD-1-blocking antibodies in cancer immunotherapy", J Leukocyte Biol, vol. 94, Jul. 2013, pp. 41-53.

Chaplin et al., "Antivascular approaches to solid tumour thereapy: evaluation of tubulin binding agents", Br. J. Cancer 1996, 74 (Suppl. XXVII), S86-S88.

Cole, P., "DURVALUMAB, Human anti-PD-L1 monoclonal antibody Immune checkpoint inhibitor Oncolytic", Drugs of the Future 2014, 39(12): pp. 843-847.

Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.

(56) References Cited

OTHER PUBLICATIONS

Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.

Cui et al. "Novel Mammalian Cell Cycle Inhibitors, Tryprostatins A, B and Other Diketopiperazines Produced by Aspergillus fumigatus." J. Antibiotics. 49(6), 534-40 (1996).

Cui et al. "Novel Mammalian Cell Cycle Inhibitors, Tryprostatins A, B and Other Diketopiperazines Produced by Aspergillus fumigatus." J. Antibiotics. 49(6): 527-33 (1996).

Davis et al., ZD6126: A Novel Vascular-targeting Agent That Causes Selective Destruction of Tumor Vasculature, Cancer Research (Dec. 15, 2002) 62: 7247-7253.

Dörwald, F. "Side Reactions in Organic Synthesis" Wiley-VCH Verlag GmbH & Co. KgaA, Weinheim, (2005), book cover and preface p. IX only.

Drug Approval and Licensing Procedures in Japan 2001, 2001, pp. 243-244.

Ferrer et al., Plinabulin: tubulin polymerization inhibitor vascular-disrupting agent oncolytic, Drugs of the Future (2010), 35(1), 11-15.

Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.

Frost et al., Novel Syngeneic Pseudo-orthotopic Prostate Cancer Model: Vascular, Mitotic and Apoptotic Responses to Castration, Microvasc Research (Dec. 2004) 69: 1-9.

Fukushima et al., "Biological Activities of Albonoursin," J. Antibiotics, (1973) 26:175.

Gameiro et al., "Exploitation of differential homeostatic proliferation of T-cell subsets following chemotherapy to enhance the efficacy of vaccine-mediated antitumor responses," Cancer Immunology Immunotherapy (2011) vol. 60, No. 9, pp. 1227-1242.

Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).

Goldani et al. "Treatment of murine pulmonary mucormycosis with SCH 42427, a broad-spectrum triazole antifungal drug", Correspondence, J Antimicrob Chemother. 33, 369-372 (1994).

Goldfarb et al., "Synthesis of β-2-thienylalanine," Izvestiya Akademii Nauk SSSR, Seriya Khimicheskaya, (1958) 98-100, as abstracted by CAPLUS.

Gordon et al. "Reductive Alkylation on a Solid Phase: Synthesis of a Piperazinedione Combinatorial Library." J. Bioorg. Med. Chem. Letters. 5, 47-50 (1995).

Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.

Gridelli et al., Vascular disrupting agents: a novel mechanism of action in the battle against non-small cell lung cancer, Oncologist (2009), 14(6), 612-620.

Gura, Trisha, "Cancer Models: Systems for Identifying New Drugs are Often Faulty", Science 7(Nov. 1997) 278(5340): 1041-1042.

Hamel, E. "Antimitotic Natural Products and Their Interactions with Tubulin." Med. Res. Rev. (1996) 16(2): 207-31.

Hartwell et al. "Checkpoints: Controls that Ensure the Order of Cell Cycle Events." Science. 246, 629-34 (1989).

Hayakawa, Structure-activity relationship analysis, Japnaese Journal of Cancer and Chemotherapy, (2004), 31(4):526-528.

Hayashi et al., "Total Synthesis of Anti-microtubule Diketopiperazine Derivatives: Phenylahistin and Aurantiamine," J. Org. Chem., (2000) 65: 8402-8405.

Hayashi et al., Small peptide-based medicinal chemistry for intractable disease, Peptide Science (2009), Volume Date 2008, 45th, 139-140.

He et al., "Low-dose paclitaxel enhances the anti-tumor efficacy of GM-CSF surface-modified whole-tumor-cell vaccine in mouse model of prostate cancer," Cancer Immunology Immunotherapy (2011) vol. 60, No. 5, pp. 715-730. Abstract.

Heist et al., "Abstract C30: Phase 1/2 study of the vascular disrupting agent (VCA) plinabulin (NPI-2358) combined with docetaxel in patients with non-small cell lung cancer (NSCLC)," *Mol. Cancer Ther.*, 2009; 8(12 Suppl):C30, 2 pages.

Heist et al., "Randomized Phase 2 Trial of Plinabulin (NPI-2358) Plus Docetaxel in Patients with Advanced Non-Small Lung Cancer (NSCLC)," 2014 ASCO Annual Meeting . . . (abstr 8054) Poster Presentation. Retrieved from the internet Jul. 17, 2017: <http://meetinglibrary.asco.org/record/92548/poster>.

Heist et al., "Randomized phase 2 trial of plinabulin (NPI-2358) plus docetaxel in patients with advanced non-small cell lung cancer (NSCLC)." J. Clin. Oncol. (2014) vol. 32, No. 5s, (suppl; abstr 8054).

Helleman et al. "The International Journal of Biochemistry & Cell Biology," vol. 42, pp. 25-30 (2010).

Horak et al. "Structures of the Austalides A-E, Five Novel Toxic Metabolites from Aspergillus ustus." J Chem Soc Chem Commun. (1981) 1265-67.

http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).

Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.

Iwasaki, S. "Antimitotic Agents: Chemistry and Recognition of Tubulin Molecule." Med Res Rev. (1993) 13: 183-198.

Iwasaki, S. "Bioactive Natural Products Interfering with Microtubule Function." Kagaku to Seibutsu. 32(3): 153-159 (1994).

Johnson et al. "Kinetic Analysis of Microtubule Self-assembly in Vitro." J. Mol. Biol. 117, 1-31 (1977).

Jure-Kunkel M. et al., "Synergy between chemotherapeutic agents and CTLA-4 blockade in preclinical tumor models", Cancer Immunol. Immunother. 2013, vol. 62, pp. 1533-1545.

Kamb, Alexander, "What's wrong with our cancer models?", Nature Reviews Drug Discovery (Feb. 2005) 4: 161-165.

Kanoh et al., "(−)-Phenylahistin: A New Mammalian Cell Cycle Inhibitor Produced by Aspergillus Ustus," Bioorganic & Medicinal Chemistry Letters, (1997) 7: 2847-2852.

Kanoh et al., "(−)-Phenylahistin Arrests Cells in Mitosis by Inhibiting Tubulin Polymerization," The Journal of Antibiotics, (1999) 52: 134-141.

Kanoh et al., "Antitumor Activity of Phenylahistin in Vitro and in Vivo,"Bioscience Biotechnology Biochemistry, (1999) 63(6): 1130-1133.

Kanoh et al., "Synthesis and Biological Activities of Phenylahistin Derivatives," Bioorganic & Medicinal Chemistry, (1999) 7: 1451-1457.

Kanthou et al., Microtubule depolymerizing vascular disrupting agents: novel therapeutic agents for oncology and other pathologies, International Journal of Experimental Pathology(2009), 90(3), 284-294.

Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12):1042-1047.

Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.

Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.

Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).

Kanzaki et al., "Novel Cyclic Dipeptide Dehydrogenase and Assay Method for Its Activity," Scientific Reports of the Faculty of Agriculture, Okayama University, (1999) 88: 7-11.

(56) References Cited

OTHER PUBLICATIONS

Keepers et al. "Comparison of the Sulforhodamine B Protein and Tetrazolium (MTT) Assays for in vitro Chemosensitivity Testing." Eur. J. Cancer. 27, 897-900 (1991).
Kim et al. "Polymer attached cyclic peptides, tetrahedron: Asymmetry." 3(11):1421-1430 (1992).
Kingston, Correction to Tubulin-interactive natural products as anticancer agents, Journal of Natural Products (2011), 74(5), 1352.
Kingston, Tubulin-Interactive Natural Products as Anticancer Agents, Journal of Natural Products (2009), 72(3), 507-515.
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3: 711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones1a," The Journal of Organic Chemistry, (1967) 33: 862-864.
Kreamer K., "Immune checkpoint blockade: A New Paradigm in Treating Advanced Cancer", J. Adv. Pract. Oncol., 2014, vol. 5, pp. 418-431.
Krishan, A. "Rapid Flow Cytofluorometric Analysis of Mammalian Cell Cycle by Propidium Iodide Staining." J. Cell Biol. 66, 188-193 (1975).
Kupchan et al. "Steganacin and Steganangin, Novel Antileukemic Lignan Lactones from Steganotaenia araliacea 1-3." J. Am. Chem. Soc. (1973) 95(4): 1335-36.
Küster & Koeppenhöfer, "Über eininge Pyrrolderivate," Z. Physiol, Chem., (1927) 172:126-137.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (and how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., Colchicine site inhibitors of microtubule integrity as vascular disrupting agents, Drug Development Research (2008), 69(6), 352-358.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liwo et al. "Origin of the Ring-Ring Interaction in Cyclic Dipeptides Incorporating an Aromatic Amino Acid." Tetrahedron Lett. 26, 1873-1876 (1985).
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Luduena, R.F. "Contrasting Roles of Tau and Microtubule-associated Protein 2 in the Vinblastine-induced Aggregation of Brain Tubulin." J. Biol. Chem. 259:12890-98 (1984).
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2011), 30(3), 1065-1073.

Mita et al., "Phase 1 First-in-Human Trial of the Vascular Disrupting Agent Plinabulin (NPI-2358) in Patients with Solid Tumors or Lymphomas," Clinical Cancer Research (2010), 16(23), 5892-5899.
Mita et al., "Phase II study of docetaxel with or without plinabulin (NPI-2358) in patients with non-small cell lung cancer (NSCLC)", J. Clin. Oncol., 2010, vol. 28, No. 15 supplement. Abstract 7592, 2 pages.
Mita et al., Randomized Phase 2 Study of Docetaxel +/− Plinabulin (NPI-2358) in Patients with Non-Small Cell Lung Cancer (NSCLC), Poster Presentation at ACS Annual '10 Meeting (Jun. 4-8, 2010) 1 page.
Mitsudomi et al., "Mutations of ras genes distinguish a subset of non-small-cell lung cancer cell lines from small-cell lung cancer cell lines," Oncogene (Aug. 1991) vol. 6, No. 8, pp. 1352-1362.
Neidle, Stephen, ed., Cancer Drug Design and Discovery , 9th Edition, Elsevier/Academic Press, (2008) Chapter 18, pp. 427-431.
Nema et al. Excipients and Their Role in Approved Injectable Products: Current Usage and Future Directions, PDA J Pharm Sci and Tech 2011, 65 287-332.
Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.
Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.
Niemann et al, "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1 ," The Journal of Organic Chemistry, (1968) 33:864-866.
Pardoll et al., "The blockade of immune checkpoints in cancer immunotherapy," Nat Rev Cancer (May 4, 2016) 12(4): 252-264.
Perez, Edith A., "Paclitaxel in Breast Cancer," The Oncologist, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Roberge et al., "Antitumor Drug Fostriecin Inhibits the Mitotic Entry Checkpoint and Protein Phospatases 1 and 2A." Cancer Res. 54, 6115-21 (1994).
Roberts et al, "Trends in the Risks and Benefits to Patients with Cancer Participating in Phase 12 Clinical Trials", JAMA (2004) 292(17): 2130-2140.
Rowinsky et al, "The clinical pharmacology and use of antimicrotubule agents in cancer chemotherapeutics", Pharmacol. Ther. 1991, 52, 35-84.
Rowinsky et al. "Taxol: A Novel Investigational Antimicrotubule Agent." J. Natl. Cancer Inst. 82(15): 1247-59 (1990).
Rozali et al., "Programmed Death Ligand 2 in Cancer-Induced Immune Suppression," Clinical and Developmental Immunology (2012) Article ID 656340, pp. 1-8.
Sackett, D.L. "Podophyllotoxin, Steganacin and Combretastatin: Natural Products that Bind at the Colchicine Site of Tubulin." Pharmacol. Ther. (1993) 59: 163-228.
Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.
Scholl et al., "Synthetic Lethal Interaction between Oncogenic KRAS Dependency and the STK33 Suppression in Human Cancer Cells", Cell (May 29, 2009) 137 pp. 821-834.
Sezaki et al., "Drug Delivery Systems", Drug Development, (Jul. 1989) 13: 116, Table 2. 29.

(56) References Cited

OTHER PUBLICATIONS

Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.

Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.

Sherline et al. "Binding of Colchicine to Purified Microtubule Protein." J. Biol. Chem. 250, 5481-86 (1975).

Shi, Q et al, "Recent progress in the development of tubulin inhibitors as antimitotic antitumor agents", Curr. Pharm. Des. 1998, 4, 219-248.

Singh et al., "A novel vascular disrupting agent plinabulin triggers JNK-mediated apoptosis and inhibits angiogenesis in multiple myeloma cells," Blood (2011), 117(21), 5692-5700.

Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.

Smedsgaard et al. "Using direct electrospray mass spectrometry in taxonomy and secondary metabolite profiling of crude fungal extracts." J. Microbiol. Meth. (1996) 25: 5-17.

Sölter et al., Barettin, Revisited? Tetrahed Lttrs. (Mar. 2002) 43: 3385-3386.

Spear et al., Vascular disrupting agents (VDA) in oncology: advancing towards new therapeutic paradigms in the clinic, Current Drug Targets (2011), 12(14), 2009-2015.

Stein, J., ed. "Internal Medicine," Fourth Edition, Mosby-Year Book, Inc., (1994), Chapters 71-72, pp. 699-729.

Stenehjem et al., "PSI/PDLI inhibitors for the treatment of advanced urothelial bladder cancer," OncoTargets and Therapy (2018) 11:5973-5989.

Steyn, P.S. "The Structures of Five Diketopiperazines from Aspergillus Ustus." Tetrahedron. 29, 107-120 (1973).

Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).

Takahashi et al. "Rhizoxin binding to tubulin at the maytansine-binding site." Biochim. Biophys. Acta. 926, 215-23 (1987).

Talmadge et al., Murine models to evaluate novel and conventional therapeutic strategies for cancer., Am J Pathol, 2007, vol. 170, Issue 3, pp. 793-804.

Thorpe, Philip E., "Vascular Targeting Agents as Cancer Therapeutics," Clinical Cancer Research, vol. 10, 415-427, Jan. 15, 2004.

Tiwari et al. "A pH- and Temperature-Dependent Cycling Method that doubles the Yield of Microtubule Protein." Anal. Biochem. 215, 96-103 (1993).

Topalian et al., "Safety, Activity, and Immune Correlates of Anti-PD-1 Antibody in Cancer," N Engl J Med. (Jun. 28, 2012) 366(26):2443-2454.

Tozer et al., Tumour vascular disrupting agents: combating treatment Resistance, British Journal of Radiology (2008), 81(Spec. Iss. 1), S12-S20.

Usui et al. "Tryprostatin A, a specific and novel inhibitor of microtubule assembly." Biochem J. 333, 543-48 (1998).

Van der Waerden, B.L., "Wirksamkeits- and Konzentrationsbestimmung durch Tierversuche." Arch Exp Pathol Pharmakol. 195, 389-412, (1940).

Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).

Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.

Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.

Wang, Y. et al, "Structures of a diverse set of colchicine binding site inhibitors in complex with tubulin provide a rationale for drug discovery." FEBS Journal (2016) 283, 102-111.

Weisenberg et al. "The Colchicine-Binding Protein of Mammalian Brain and its Relation to Microtubules." Biochemistry (1968) 7(12): 4466-79.

Wilt et al. "Anal cancer in Alaska; a retrospective study of incidence, treatment, and outcomes". Alaska Med Jul.-Sep. 2002; 44(3):56-9, 62.

Yahara et al. "Microtubule Organization of Lymphocytes and its Modulation by Patch and Cap Formation." Cell. 15, 251-259 (1978).

Yamazaki et al. "Crystal Structure and Absolute Configuration of Fumitremorgin B, a Tremorgenic Toxin from Aspergillus Fumigatus Fres." Tetrahedron Lett. 1, 27-28 (1975).

Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.

Yamazaki et al., Drug discovery study on cyclic dipeptides anti-cancer drugs and chemical biological development, Idenshi Igaku Mook (2012), 21(Saishin Pepuchido Gosei Gijutsu to Sono Soyaku Kenkyu eno Oyo), 260-266.

Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.

Yin et al., "Human Mutations That Confer Paclitaxel Resistance," Mol. Cancer Ther. vol. 9(2), pp. 327-335 (2010).

Yokio et al, "Neihumicin, A New Cytotoxic Antibiotic From Micromonospora Neihuensis," The Journal of Antibiotics, (Apr. 1988) 41(4):494-501.

Yoshida, M.M. Protein Nucleic Acid Enzymes. 38, 1753-1765 (1993).

Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).

Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.

Zheng, Lei, "Does vaccine-primed pancreatic cancer offer better candidates for immune-based therapies?" Immunotherapy (2014) 6(10):1017-1020.

Agarwal et al., "OP449, a Novel SET Antagonist, Is Cytotoxic to Leukemia Cells and Enhances Efficacy of Tyrosine Kinase Inhibitors in Drug-Resistant Myeloid Leukemias," pursuant to an EMBASE record for a Conference Abstract: 603. Oncogenes and Tumor Suppressors: Poster II (Nov. 15, 2013) Blood (2013) 122(21): 2511.

Braga et al. "Crystal Polymorphism and Multiple Crystal Forms," Struct Bond (2009) 132:25-50.

Caira, 1998, Crystalline polymorphism of organic compounds, Topics in Current Chemistry, 198:163-208.

Carter et al., "No patient left behind: The promise of immune priming with epigenetic agents," Oncoimmunology (2017) vol. 6, No. 10, e1315486 (13 pages).

Chen et al., "Adjuvant effect of docetaxel on the immune responses to influenza a H1N1 vaccine in mice," BMC Immunology (2012) 13:36, pp. 1-12.

Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.

ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltrials.gov/ct2/show/NCT00892931> 7 pages.

ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from

(56) References Cited

OTHER PUBLICATIONS

Internet on Sep. 17, 2019], <URL: https://clinicaltrials.gov/ct2/show/NCT02846792?term=plinabuilin&rank=1> 11 pages.

Dunitz et al., "Disappearing Polymorphs," Acc. Chem. Res. (1995) vol. 28, No. 4, pp. 193-200.

Fernandez-Medarde et al., Mar. 2011, Ras in cancer and developmental diseases, Genes & Cancer, 2(3):344-358.

Gallina et al., "Condensation of 1,4-diacetylpiperazine-2,5-dione with aldehydes", Tetrahedron 1974, 30, 667-673.

Gu et al., "Identification of CTLA-4 isoforms produced by alternative splicing and their association with myasthenia gravis," Clinical Immunology (Sep. 2008) vol. 128, Issue 3, pp. 374-381.

Hayashi et al., Medicinal chemistry and chemical biology of diketopiperazine-type antimicrotubule and vascular-disrupting agents, Chemical & Pharmaceutical Bulletin (2013), 61(9), 889-901.

Hursthouse et al., "Why Do Organic Compounds Crystallise Well or Badly or Ever so Slowly? Why Is Crystallisation Nevertheless Such a Good Purification Technique?," Organic Process Res & Devel (2009) vol. 13, No. 6, pp. 1231-1240.

Ji et al., Tubulin Colchicine Binding Site Inhibitors as Vascular Disrupting Agents in Clinical Developments, Current Medicinal Chemistry (2015), 22(11), 1348-1360.

Jiang et al., "A Novel Peptide Isolated from a Phage Display Peptide Library with Trastuzumab Can Mimic Antigen Epitope of HER-2*," (Feb. 11, 2005) J Biol Chem, vol. 280, No. 6, pp. 4656-4662.

Kakoulidou et al., "Human Soluble CD80 is Generated by Alternative Splicing, and Recombinant Soluble CD80 Binds to CD28 and CD152 Influencing T-cell Activation," Scandinavian J. Immunol (Nov. 2007) 66(5):529-537.

Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.

Lee et al., "A practical guide to pharmaceutical polymorph screening & selection," Asian Journal of Pharmaceutical Sciences (2014) vol. 9, pp. 163-175.

Liao et al., "Design and synthesis of novel soluble 2,5-diketopiperazine derivatives as potential anticancer agents," European J Med Chem (2014) 83:236-244.

Lu et al., Nov. 2012, An overview of tubulin inhibitors that interact with the colchicine binding site, Pharmaceutical Research, 29(11):2943-2971.

Lyman et al., "Risk Models for Predicting Chemotherapy-Induced Neutropenia," The Oncologist (2005) 10:427-437.

Lynch et al., "Ipilimumab in Combination With Paclitaxel and Carboplatin As First-Line Treatment in Stage IIIB/IV Non-Small-Cell Lung Cancer: Results From a Randomized, Double-Blind, Multicenter Phase II Study," (Jun. 10, 2012) J Clin Oncol, vol. 30, No. 17, pp. 2046-2054.

Mahindroo et al., "Antitubulin Agents for the Treatment of Cancer—A Medicinal Chemistry Update", Expert Opin. Ther. Patents (2006) 16(5): 647-691.

Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.

Matsuda et al., "Pilot study of WT1 peptide-pulsed dendritic cell vaccination with docetaxel in esophageal cancer," Oncology Letters (Jul. 2018) vol. 16, No. 1, pp. 1348-1356.

Millward et al., "Phase I trial of NPI-2358 (a novel vascular disrupting agent) plus docetaxel," J. Clin. Oncol. (May 2009) 27(15S): 3571-3571, Abstract.

Mohanlal et al., "The plinabulin/docetaxel combination to mitigate the known safety concerns of docetaxel," J Clin Oncol (2016) 34(15_suppl), Abstract e20595.

Muguruma et al., OP-20: "Application of Fc-selective Z33-peptide to the preparation of non-covalent-type antibody-antimocrotubule plinabulin conjugate," 34th European Peptide Symposium 2016 & 8th International Peptide Symposium, Journal of Peptide Sci (Sep. 5, 2016—5:30pm) 22 Supplement 2 ISSN: 1099-1387 in English (Oral Presentation). Abstract.

Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," NEOPLASIA (Aug. 2013) vol. 15, No. 8, pp. 939-951.

Ohaegbulam et al., "Human cancer immunotherapy with antibodies to the PD-1 and PD-L1 pathway," Trends Mol Med, (Oct. 30, 2014) 21(1): pp. 24-33.

Ott et al., "CTLA-4 and PD-1/PD-L1 Blockade: New Immunotherapeutic Modalities with Durable Clinical Benefit in Melanoma Patients," Clin Cancer Res (Oct. 1, 2013) 19(19): pp. 5300-5309.

Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.

Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, pp. 16667-16674.

Prior et al., "A Comprehensive Survey of Ras Mutations in Cancer" Cancer Res. (2012) vol. 72, No. 10, pp. 24570-2467.

Raza et al., 2014, Polymorphism: the phenomenon affecting the performance of drugs, SOJ Pharmacy & Pharmaceutical Sciences, 10 pp.

Reck, M., "What future opportunities may immuno-oncology provide for improving the treatment of patients with lung cancer?" (2012) Annals of Oncology (Sep. 2012) 23 (Supp. 8) viii28-viii34.

Remington, "The Science and Practice of Pharmacy, 20th Ed" (2000) p. 709.

Rhodes, John, "Section Review: Biologicals & Immunologicals: Therapeutic potential of Schiff base-forming drugs," Expert Opinion on Investigational Drugs (1996) vol. 5, Issue 3, pp. 257-268.

Riemer et al., "Matching of trastuzumab (Herceptin®) epitope mimics onto the surface of Her-2/neu—a new method of epitope definition," Mol Immunol 42 (2005) pp. 1121-1124.

Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.

Turner et al. "Recent Advances in the Medicinal Chemistry of Antifungal Agents." Current Pharmaceutical Design. 2, 209-224 (1996).

University of Washington, "Nivolumab and Plinabuilin in Treating Patients With Stage IIIB-IV, Recurrent, or Metastatic Non-small Cell Lung Cancer," Clinical trial study first posted Jul. 27, 2016. URL:https://clinicaltrials.gov/ct2/show/ NCT02846792.

US Food and Drug Administration, Highlights of prescribing information, retrieved Apr. 16, 2020 from https://www.accessdata.fda.gov/drugsatfda_docs/label/2015/125031s180lbl.pdf, Rev. Nov. 2015, Reference ID:4192944.

Yamato et al., "Clinical importance of B7-H3 expression in human pancreatic cancer," British Journal of Cancer (Oct. 20, 2009) 101, pp. 1709-1716.

Yamori T., "A Human Cell Line Panel for Screening Anti-Cancer Drugs", Jap. J. Cancer Chemother. 24, 129-35 (1997).

Yang et al., "The KRAS Mutation is Highly Correlated With EGFR Alterations in Patients With Non-small Cell Lung Cancer," Fooyin J Health Sci (2009) vol. 1(2): pp. 65-71.

Younis et al., 2011, The cost-utility of adjuvant chemotherapy using docetaxel and cylophosphamide compared with doxorubicin and cyclophosphamide in breast cancer, Current Oncology 18(8):e298-3296.

Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.

International Search Report and Written Opinion dated May 19, 2016 for PCT/US2016/020390.

* cited by examiner

METHOD OF TREATING CANCER ASSOCIATED WITH A RAS MUTATION

CROSS-REFERENCE TO RELATED APPLICATIONS

This application is a continuation of U.S. application Ser. No. 16/290,765, filed on Mar. 1, 2019, which is a continuation of U.S. application Ser. No. 15/555,963, filed on Sep. 5, 2017, which was the National Phase of International Application No. PCT/US2016/020390, filed on Mar. 2, 2016 and published on Sep. 15, 2016 as WO 2016/144635, which claims the benefit of U.S. Provisional Application No. 62/129,654, filed on Mar. 6, 2015, and U.S. Provisional Application No. 62/249,788, filed on Nov. 2, 2015, the disclosures of which are incorporated herein by reference in their entireties.

BACKGROUND

Field

The present invention relates to the field of chemistry and medicine. More particularly, the present invention relates to method of treating cancer associated with a RAS mutation using Plinabulin.

Description of the Related Art

RAS proteins function as binary molecular switches that control intracellular signaling networks. RAS-regulated signal pathways control processes such as actin cytoskeletal integrity, proliferation, differentiation, cell adhesion, apoptosis, and cell migration. The RAS subfamily includes at least 21 members such as KRAS, NRAS, and HRAS. RAS or RAS-related protein relay signals from outside the cell to the cell's nucleus. These signals instruct the cell to grow and divide or to mature and take on specialized functions (differentiate). The RAS proteins belong to a class of protein called GTPase, which means it converts a molecule called GTP into another molecule called GDP. A RAS protein acts like a switch, and it is turned on and off by the GTP and GDP molecules. To transmit signals, the RAS protein must be turned on by attaching (binding) to a molecule of GTP. A RAS protein is turned off (inactivated) when it converts the GTP to GDP. When the protein is bound to GDP, it does not relay signals to the cell's nucleus. When a RAS protein is mutated at certain codons, the RAS protein is stuck in its GTP bound state, so it keeps sending signal to nucleus and the cell could not stop dividing, which is un-controlled cell growth or cancer.

The RAS genes belong to a class of genes known as oncogenes. A mutant form of RAS gene has the potential to cause normal cells to become cancerous. The proteins produced from these RAS genes are GTPases. These proteins play important roles in cell division, cell differentiation, and the cell apoptosis. However, the mechanisms by which oncogenic RAS coordinates the shift in metabolism to sustain tumor growth, particularly in the tumor microenvironment, and whether specific metabolic pathways are essential for RAS-mediated tumor maintenance remain areas of active investigation. Cancers characterized by a RAS mutation are difficult to treat using known therapies, and there are no approved drugs for treating these cancers. RAS mutation is a negative predictor of cancer patient survival; cancer patients have much poorer prognostic outcome (or shorter overall survival) when their cancer has RAS mutation. Thus, there is a dire unmet need for a more effective treatment for cancer associated with oncogenic RAS gene mutation.

SUMMARY

Some embodiments relate to a method of treating a cancer characterized by expressing a mutant form of RAS protein, comprising administering Plinabulin to a subject in need thereof.

Some embodiments relate to a method of treating a cancer characterized by expressing a mutant form of KRAS protein, comprising administering Plinabulin to a subject in need thereof.

Some embodiments relate to a method of treating a cancer characterized by expressing a mutant form of NRAS protein, comprising administering Plinabulin to a subject in need thereof.

Some embodiments relate to a method of inhibiting proliferation of a cell having a RAS mutation, comprising contacting the cell with Plinabulin.

Some embodiments relate to a method of inducing apoptosis in a cell having a RAS mutation, comprising contacting the cell with Plinabulin.

Some embodiments relate to a method of inhibiting progression of a cancer characterized by expressing a mutant form of RAS protein in a subject, comprising administering Plinabulin to a subject in need thereof.

BRIEF DESCRIPTION OF THE DRAWINGS

FIG. 1a shows T2 MRI images of a human GBM that display peritumoral edema; and FIG. 1b shows T2 MRI images of mouse GBM that display peritumoral edema; FIG. 1c shows human micrograph images of H&E stains of a GBM showing hallmark pseudopalisading necrosis and microvascular proliferation; FIG. 1d shows mouse micrograph images of H&E stains of a GBM showing hallmark pseudopalisading necrosis and microvascular proliferation.

DETAILED DESCRIPTION OF THE PREFERRED EMBODIMENT

Figure 1:
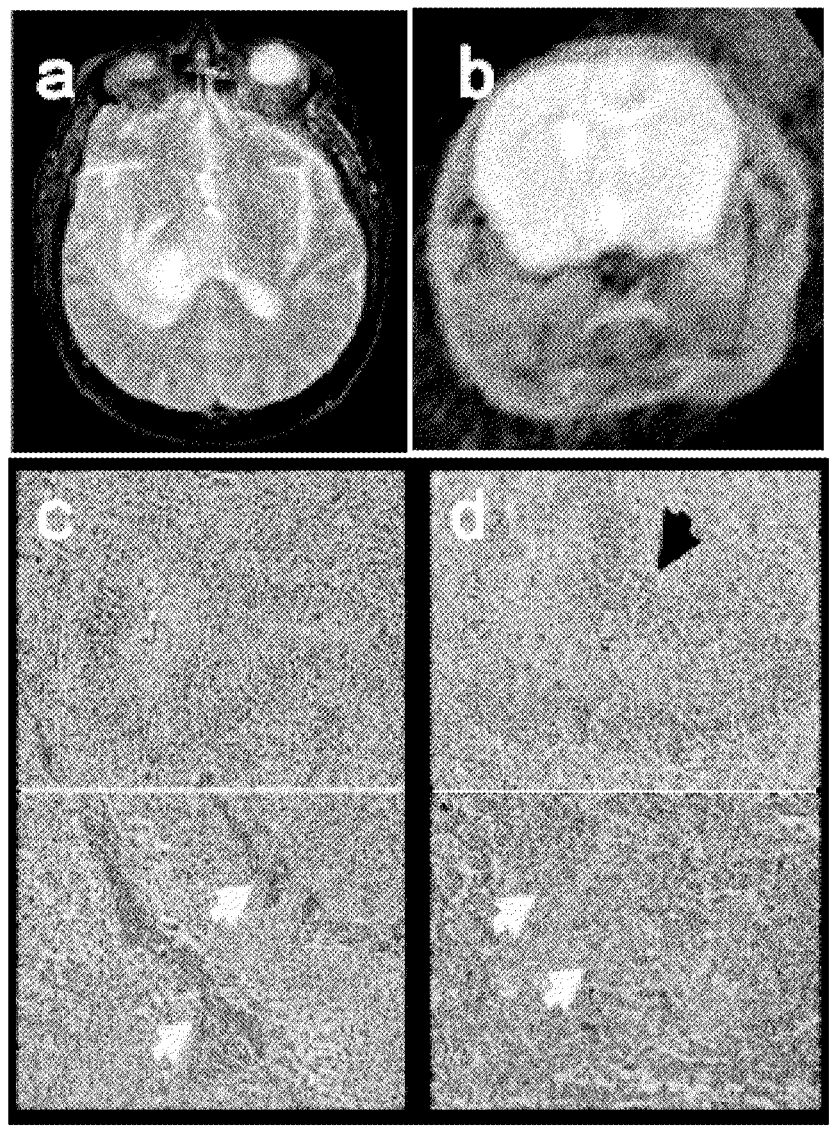
FIGS. 1a-1d show the proneural genetically engineered murine model (GEMM) of glioblastoma (GBM) that mimics human pathology.

Plinabulin, (3Z,6Z)-3-Benzylidene-6-{[5-(2-methyl-2-propanyl)-1H-imidazol-4-yl]methylene}-2,5-piperazinedione, is a synthetic analog of the natural compound phenylahistin. Plinabulin can be readily prepared according to methods and procedures detailed in U.S. Pat. Nos. 7,064,201 and 7,919,497, which are incorporated herein by reference in their entireties. Some embodiments relate to the use of Plinabulin to treat cancer associated with an oncogenic RAS mutation. Some embodiments relate to the use of Plinabulin to treat a cancer characterized by expressing a mutant form of RAS protein in a subject. Some embodiments relate to the use of Plinabulin to inhibit proliferation of a cell having a RAS mutation. Some embodiments relate to the use of Plinabulin to induce apoptosis in a cell having a RAS mutation. Some embodiments relate to the use of Plinabulin to inhibit progression of a cancer that is characterized by expressing a mutant form of RAS protein in a subject. In some embodiments, the RAS protein is a KRAS protein. In some embodiments, the RAS protein is a NRAS protein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

In some embodiments, the composition can further include one or more pharmaceutically acceptable diluents. In some embodiments, the pharmaceutically acceptable diluent can include kolliphor® (Polyethylene glycol (15)-hydroxystearate). In some embodiments, the pharmaceutically acceptable diluent can include propylene glycol. In some embodiments, the pharmaceutically acceptable diluents can include Kolliphor® HS15 and propylene glycol. In some embodiments, the pharmaceutically acceptable diluents can include Kolliphor® HS15 and propylene glycol, wherein the Kolliphor® HS15 is about 40% by weight and propylene glycol is about 60% by weight based on the total weight of the diluents. In some embodiments, the composition can further include one or more other pharmaceutically acceptable excipients.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of Plinabulin or pharmaceutically acceptable salts thereof; and (b) a pharmaceutically acceptable carrier, diluent, excipient or combination thereof.

Other embodiments include co-administering Plinabulin and an additional therapeutic agent in separate compositions or the same composition. Thus, some embodiments include a first pharmaceutical composition comprising: (a) a safe and therapeutically effective amount of Plinabulin or pharmaceutically acceptable salts thereof and (b) a pharmaceutically acceptable carrier, diluent, excipient or combination thereof; and a second pharmaceutical composition comprising: (a) a safe and therapeutically effective amount of an additional therapeutic agent and (b) a pharmaceutically acceptable carrier, diluent, excipient or combination thereof. Some embodiments include a pharmaceutical composition comprising: (a) a safe and therapeutically effective amount of Plinabulin or pharmaceutically acceptable salts thereof; (b) a safe and therapeutically effective amount of an additional therapeutic agent; and (c) a pharmaceutically acceptable carrier, diluent, excipient or combination thereof.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably a mammalian subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, sublingual, buccal, nasal, rectal, topical (including transdermal and intradermal), ocular, intracerebral, intracranial, intrathecal, intraarterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g., liquid gel capsule and solid gel capsule), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium (EDTA), although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one or more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a single dose of Plinabulin or other therapeutic agent may be from about 5 mg/m$^2$ to about 150 mg/m$^2$ of body surface area, from about 5 mg/m$^2$ to about 100 mg/m$^2$ of body surface area, from about 10 mg/m$^2$ to about 100 mg/m$^2$ of body surface area, from about 10 mg/m$^2$ to about 80 mg/m$^2$ of body surface area, from about 10 mg/m$^2$ to about 50 mg/m$^2$ of body surface area, from about 10 mg/m$^2$ to about 40 mg/m$^2$ of body surface area, from about 10 mg/m$^2$ to about 30 mg/m$^2$ of body surface area, from about 13.5 mg/m$^2$ to about 100 mg/m$^2$ of body surface area, from about 13.5 mg/m² to about 80 mg/m² of body surface area, from about 13.5 mg/m² to about 50 mg/m² of body surface area, from about 13.5 mg/m² to about 40 mg/m² of body surface area, from about 13.5 mg/m² to about 30 mg/m² of body surface area, from about 15 mg/m² to about 80 mg/m² of body surface area, from about 15 mg/m² to about 50 mg/m² of body surface area, or from about 15 mg/m² to about 30 mg/m² of body surface area. In some embodiments, a single dose of Plinabulin or other therapeutic agent may be from about 13.5 mg/m² to about 30 mg/m² of body surface area. In some embodiments, a single dose of Plinabulin or other therapeutic agent may be about 5 mg/m², about 10 mg/m², about 12.5 mg/m², about 13.5 mg/m², about 15 mg/m², about 17.5 mg/m², about 20 mg/m², about 22.5 mg/m², about 25 mg/m², about 27.5 mg/m², about 30 mg/m², about 40 mg/m², about 50 mg/m², about 60 mg/m², about 70 mg/m², about 80 mg/m², about 90 mg/m², or about 100 mg/m², of body surface area.

In some embodiments, a single dose of Plinabulin or other therapeutic agent may be from about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg, In some embodiments, a single dose of Plinabulin or other therapeutic agent may be from about 20 mg to about 60 mg, from about 27 mg to about 60 mg, from about 20 mg to about 45 mg, or from about 27 mg to about 45 mg. In some embodiments, a single dose of Plinabulin or other therapeutic agent may be about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

The administration period can be a multi-week treatment cycle as long as the tumor remains under control and the regimen is clinically tolerated. In some embodiments, a single dosage of Plinabulin or other therapeutic agent can be administered once a week, and preferably once on each of day 1 and day 8 of a three-week (21 day) treatment cycle. In some embodiments, a single dosage of Plinabulin or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

In some embodiments, the compositions described herein can be used in combination with other therapeutic agents. In some embodiments, the compositions described herein can be administered or used in combination with treatments such as chemotherapy, radiation, and biologic therapies.

Methods of Treatment

Some embodiments relate to a method of treating a cancer characterized by expressing a mutant form of a RAS protein, comprising administering Plinabulin to a subject in need thereof. Some embodiments relate to a method of treating a cancer associated with an oncogenic RAS mutation, comprising administering Plinabulin to a subject in need thereof.

In some embodiments, the mutant form of the RAS protein is a mutant form of a KRAS, NRAS, or HRAS protein. In some embodiments, the RAS protein is a KRAS, NRAS, or HRAS protein. In some embodiments, the mutant form of the RAS is a mutant form of the KRAS protein. In some embodiments, the mutant form of the RAS is a mutant form of the NRAS protein. In some embodiments, the RAS gene mutation is KRAS gene mutation. In some embodiments, the RAS gene mutation is NRAS gene mutation.

Some embodiments relate to a method of treating a cancer characterized by expressing a mutant form of a KRAS protein, comprising administering Plinabulin to a subject in need thereof. Some embodiments relate to a method of treating a cancer associated with an oncogenic KRAS mutation, comprising administering Plinabulin to a subject in need thereof.

Some embodiments relate to a method of treating a cancer characterized by expressing a mutant form of a NRAS protein, comprising administering Plinabulin to a subject in need thereof. Some embodiments relate to a method of treating a cancer associated with an oncogenic NRAS mutation, comprising administering Plinabulin to a subject in need thereof.

Some embodiments of the present invention include methods of treating cancer with Plinabulin and compositions comprising Plinabulin described herein. Some methods include administering a compound, composition, pharmaceutical composition described herein to a subject in need thereof. In some embodiments, a subject can be an animal, e.g., a mammal, a human.

In some embodiments, cancer is selected from colorectal cancer, pancreatic cancer, renal caner, lung cancer, liver cancer, breast cancer, prostate cancer, gastrointestinal cancer, peritoneal cancer, melanoma, endometrial cancer, ovarian cancer, cervical cancer, uterine carcinoma, bladder cancer, glioblastoma, brain metastases, salivary gland carcinoma, thyroid cancer, brain cancer, lymphoma, myeloma, and head and neck cancer. In some embodiments, the cancer is selected from squamous cell cancer, small-cell lung cancer, non-small cell lung cancer, adenocarcinoma of the lung, squamous carcinoma of the lung, hepatocellular carcinoma, colon cancer, endometrial carcinoma, and hepatocellular carcinoma. In some embodiments, the cancer is selected from colorectal cancer, prostate cancer, breast cancer, lung cancer, endometrial cancer, multiple myeloma, pancreatic, renal cancer, and glioblastoma. In some embodiments, the cancer is selected from non-small cell lung cancer, pancreatic cancer, and glioblastoma. In some embodiments, the cancer is non-small cell lung cancer.

In some embodiments, the KRAS comprises mutation at one or more positions selected from codons 12, 13, 59, and 61. In some embodiments, the mutant form of the KRAS protein has mutation at one or more amino acid positions selected from G12, G13, S17, P34, A59, and Q61. In some embodiments, the mutant form of the KRAS protein has one or more amino acid substitutions selected from the group consisting of G12C, G12S, G12R, G12F, G12L, G12N, G12A, G12D, G12V, G13C, G13S, G13D, G13V, G13P, S17G, P34S, A59E, A59G, A59T, Q61K, Q61L, Q61R, and Q61H. In some embodiments, the mutant form of the KRAS protein has mutation at one or more amino acid positions selected from G12, G13, A59, Q61, K117 and A146. In some embodiments, the mutant form of the KRAS protein has one or more amino acid substitutions selected from the group consisting of G12C, G12R, G12S, G12A, G12D, G12V, G13C, G13R, G13S, G13A, G13D, G13V, A59E, A59G, A59T, Q61K, Q61L, Q61R, Q61H, K117N, K117R, K117E, A146P, A146T and A146V. In some embodiments, the mutant form of the KRAS protein has mutation at one or more amino acid positions selected from of G12, G13, A59 and Q61. In some embodiments, the mutant form of the KRAS protein has one or more amino acid substitutions selected from the group consisting of G12C, G12R, G12S, G12A, G12D, G12V, G13C, G13R, G13S, G13A, G13D, A59E, A59G, A59T, Q61K, Q61L, Q61R and Q61H. In some embodiments, the mutant form of the KRAS protein has mutation at one or more amino acid positions selected from G12, G13, and D153. In some embodiments, the mutant form of the KRAS protein has one or more amino acid substitutions selected from the group consisting of G12A, G12C, G12D, G12V, G12S, G13D, and D153V. In some embodiments, the mutant form of the KRAS protein has one or more amino acid substitutions selected from G12C, G12S, and D153V.

In some embodiments, the NRAS comprises mutation at one or more positions selected from codons 12, 13, 59, 61, and 146. In some embodiments, the mutant form of the KRAS protein has mutation at one or more amino acid positions selected from G12, G13, A59, Q61, K117 and A146. In some embodiments, the mutant form of the KRAS protein has one or more amino acid substitutions selected from the group consisting of G12C, G12R, G12S, G12A, G12D, G12V, G13C, G13R, G13S, G13A, G13D, G13V, A59D, A59T, Q61K, Q61L, Q61R, Q61H, K117N, K117R, K117E, A146P, A146T and A146V. In some embodiments, the mutant form of the NRAS protein has mutation at one or more amino acid positions at Q61 or A146. In some embodiments, the mutant form of the NRAS protein has one or more amino acid substitutions selected from Q61K, Q61H, Q61R, Q61L, Q61N, Q61E, Q61P, A146T, A146P, A146V, and any combinations thereof. In some embodiments, the mutant form of the NRAS protein has one or more amino acid substitutions selected from Q61H, Q61R, Q61L, and any combinations thereof.

Some embodiments relate to a method of inhibiting proliferation of a cell having a RAS mutation, comprising administering Plinabulin to a subject in need thereof. Some embodiments relate to a method of inducing apoptosis in a cell having a RAS mutation, comprising contacting the cell with Plinabulin. In some embodiments, the contacting includes administering Plinabulin to a subject in need thereof. Some embodiments relate to a method of inhibiting progression of a cancer characterized by expressing a mutant form of RAS in a subject, comprising contacting the cell with Plinabulin. In some embodiments, the contacting includes administering Plinabulin to a subject in need thereof.

Some embodiments relate to a method of inhibiting proliferation of a cell having a KRAS mutation, comprising administering Plinabulin to a subject in need thereof. Some embodiments relate to a method of inducing apoptosis in a cell having a KRAS mutation, comprising contacting the cell with Plinabulin. Some embodiments relate to a method of inhibiting progression of a cancer characterized by expressing a mutant form of KRAS in a subject, comprising contacting the cell with Plinabulin.

Some embodiments relate to a method of inhibiting proliferation of a cell having a NRAS mutation, comprising administering Plinabulin to a subject in need thereof. Some embodiments relate to a method of inducing apoptosis in a cell having a NRAS mutation, comprising contacting the cell with Plinabulin. Some embodiments relate to a method of inhibiting progression of a cancer characterized by expressing a mutant form of NRAS in a subject, comprising contacting the cell with Plinabulin.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

The treatment method described herein can include co-administering Plinabulin with an additional active agent. In some embodiments, the method further includes administering an additional therapeutic agent. In some embodiments, the additional therapeutic agent is docetaxel and the cancer is human non-small cell lung cancer. In some embodiments, the additional therapeutic agent is Bevacizumab and the cancer is human non-small cell lung cancer. In some embodiments, the additional therapeutic agent is Irinotecan and the cancer is colon cancer. In some embodiments, the additional therapeutic agent is Temolozomide and the cancer is glioblastoma. In some embodiments, the additional therapeutic agent is irinotecan and the cancer is colon cancer.

In some embodiments, the additional therapeutic agent can be temozolomide, bevicizumab, everolimus, carmustine, lomustine, procarbazine, vincristine, irinotecan, cisplatin, carboplatin, methatrexate, etoposide, vinblasatine, bleomycin, actinomycin, cyclophosphamide, or ifosfamide. In some embodiments, the additional therapeutic agent is selected from bevacizumab, docetaxel, Irinotecan, and temozolomide. In some embodiments, the additional therapeutic agent is docetaxel. In some embodiments, the additional therapeutic agent is irinotecan. In some embodiments, the additional therapeutic agent is bevacizumab. In some embodiments, the additional therapeutic agent is temozolomide. In some embodiments, the additional therapeutic agent is gemcitabine. In some embodiments, the additional therapeutic agent is carmustine. In some embodiments, the additional therapeutic agent is lomustine.

The treatment method described herein can also be used in combination with a radiation therapy.

The method described herein can further include identifying a patient having a cancer characterized by expressing a mutant type of RAS protein. In some embodiments, identifying a patient can include determining whether the patient has a RAS mutation. Some embodiments relate to a method for treating cancer in a patient identified as having a RAS mutation, the method comprising administering to the patient a pharmaceutically effective amount of Plinabulin, wherein the patient has been identified by (i) collecting a sample from the patient; (ii) isolating DNA from the sample; (iii) amplifying a RAS gene or fragment thereof in the isolated DNA; and (iv) detecting whether there is a mutation in the amplified RAS gene, thereby determining whether the patient has a cancer characterized by a RAS mutation. Examples of methods for detecting RAS mutation include but are not limited to Amplified Refractory Mutation System (ARMS) PCR, BEAMing assays, digital PCR, and other suitable primers, and probes for sequencing or PCR.

The method described herein can further include identifying a patient having a cancer characterized by expressing a mutant type of KRAS. In some embodiments, identifying a patient can include determining whether the patient has a KRAS mutation. Some embodiments relate to a method for treating cancer in a patient identified as having a KRAS mutation, the method comprising administering to the patient a pharmaceutically effective amount of Plinabulin, wherein the patient has been identified by (i) collecting a sample from the patient; (ii) isolating DNA from the sample; (iii) amplifying a KRAS gene or fragment thereof in the isolated DNA; and (iv) detecting whether there is a mutation in the amplified KRAS gene, thereby determining whether the patient has a cancer characterized by a KRAS mutation.

The method described herein can further include testing for a KRAS mutation. In some embodiments, KRAS mutations, e.g., at codons 12, 13, 59, 61 and/or 146 may be detected from pathology samples taken from the patient. In some embodiments of such testing, DNA is removed from the sample and tested against labeled oligonucleotide probes using PCR to amplify the targeted mutated DNA to permit detection. In some embodiments, commercial testing centers can carry out such tests. In some embodiments, a test kit such as the TheraScreen: K-RAS Mutation kit (DxS Ltd, 48 Grafton Street, Manchester Ml 3 9XX, UK) may be used. For example, the TheraScreen kit can detect mutations in codons 12 and 13 of the K-RAS oncogene:

GIy 12 Asp (GGT>GAT) GIy 12 Arg (GG1>CGT)
GIy 12 Ala (GGT>GCT) GIy 12Cy s (GGT>TGT)
GIy 12Val (GGT>GTT) GIy 13 Asp (GGOGAC)
Glyl2Ser (GGT>AGT)

The method described herein can further include identifying a patient having a cancer characterized by expressing a mutant type of NRAS protein. In some embodiments, identifying a patient can include determining whether the patient has a NRAS mutation. Some embodiments relate to a method for treating cancer in a patient identified as having a NRAS mutation, the method comprising administering to the patient a pharmaceutically effective amount of Plinabulin, wherein the patient has been identified by (i) collecting a sample from the patient; (ii) isolating DNA from the sample; (iii) amplifying a NRAS gene or fragment thereof in the isolated DNA; and (iv) detecting whether there is a mutation in the amplified NRAS gene, thereby determining whether the patient has a cancer characterized by a NRAS mutation.

The method described herein can further include testing for a NRAS mutation. In some embodiments, NRAS mutations, e.g., at codons 12, 13, 59, 61 and/or 146, may be detected from pathology samples taken from the patient. In some embodiments of such testing, DNA is removed from the sample and tested against labeled oligonucliotide probes using PCR to amplify the targeted mutated DNA to permit detection. Several commercially available kits (see Dxs Diagnostic Innovations, Applied Biosystems, and Quest diagnostics), primers and probes for sequencing or PCR can be designed based on the codon mutations of NRAS.

The method described herein can further include identifying a patient having a cancer characterized by expressing a mutant type of HRAS protein. In some embodiments, identifying a patient can include determining whether the patient has a HRAS mutation. Some embodiments relate to a method for treating cancer in a patient identified as having a HRAS mutation, the method comprising administering to the patient a pharmaceutically effective amount of Plinabulin, wherein the patient has been identified by (i) collecting a sample from the patient; (ii) isolating DNA from the sample; (iii) amplifying a HRAS gene or fragment thereof in the isolated DNA; and (iv) detecting whether there is a mutation in the amplified HRAS gene, thereby determining whether the patient has a cancer characterized by a HRAS mutation.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1

All cell lines were grown in their respective proper growth media supplemented with 2-10% FBS and were housed in an atmosphere of 5% $CO_2$ at 37° C.

Cells were plated in growth media in 96-well microtiter plates at a 100 uL volume. Cells were then incubated for 24 hours at 37° C. in a humidified incubator. The test agent (Plinabulin)'s doses were achieved using HP D300 Digital Dispenser. Briefly, the digital dispenser added test agent (Plinabulin) in a DMSO solvent at precise volumes to media containing wells. Control wells received equivolumes of DMSO that test agent (Plinabulin) wells received. Following addition of the test agents, cells were exposed at the concentrations and dilutions described in Table 1 for 72 hours at 37° C. in a humidified incubator. Following 72 hour exposure, Plinabulin and control media were removed and 200 μl of a 1:1 mixture of media and CellTiter-Glo® Reagent was added to each well. The plates were incubated for 60 minutes at 37° C. in a humidified incubator. After incubation, luminescence was recorded using a luminometer.

TABLE 1

Single Agent Cell Viability Assay

| Test Agents Concentrations | 1 μM high: 10 concentrations; 1:3 dilutions* |
|---|---|
| Standard Agent Concentrations | 1-100 μM high[1]: 10 concentrations; 1:3 dilutions[2] |
| Assay Exposure Time | 72 hours continuous |

TABLE 1-continued

Single Agent Cell Viability Assay

| Method | CellTiter-Glo ® Cell Viability Assay |
|---|---|
| Replicates | 3 replicates per concentration; 2 technical replicates |

[1] Concentrations and dilution factor may be changed after initial screen to optimize curve fitting.
[2] High concentration were selected based on the expected activity of the respective SOC.

Data were expressed as the percent cell growth of the untreated (vehicle) control calculated from the luminescence signals. The surviving fraction of cells was determined by dividing the mean luminescence values of the samples treated with Plinabulin by the mean luminescence values of untreated control. The inhibitory concentration ($IC_{50}$) value for the Plinabulin treated sample and control were estimated using Prism 6 software (GraphPad Software, Inc.) by curve-fitting the data using the non-linear regression analysis.

TABLE 2

Summary of Plinabulin $IC_{50}$ results for various cancer cell lines with RAS mutant

| Cells | RAS mutant | Tissue Type | $IC_{50}$ (nM) |
|---|---|---|---|
| KMS-27 | NRAS (p.Q61R) | Human Multiple Myeloma | 7.84 |
| MOLP-8 | NRAS (p.Q61L) | Human Multiple Myeloma | 4.22 |
| MM.1S | KRAS (p.G12A) | Human Multiple Myeloma | 18.99 |
| L363 | NRAS (p.Q61H) | Human Multiple Myeloma | 9.44 |
| SNG-M | KRAS(p.G12V) | Human Endometrial | 13.08 |
| HEC1a | KRAS(p.G12D) | Human Endometrial | 57.74 |
| HCT-15 | KRAS(p.G13D) | Human Colorectal | 13.08 |
| LoVo | KRAS(p.G13D) | Human Colorectal | 6.85 |
| HCT116 | KRAS(p.G13D) | Human Colorectal | 32.75 |
| RXF-393 | KRAS(p.D153V) | Human Renal | 4.37 |
| AsPC-1 | KRAS(p.G12D) | Human Pancreatic | 16.92 |
| Capan-2 | KRAS(p.G12V) | Human Pancreatic | 10.33 |
| MIA PaCa-2 | KRAS(p.G12C) | Human Pancreatic | 92.31 |

As shown in Table 2, Plinabulin as a single active agent has cytotoxic effects at low $IC_{50}$ concentrations on various tumor cell lines with a RAS mutation, including both KRAS and NRAS mutations.

Example 2

The combination of Plinabulin and Docetaxel was tested and its activity compared to the standard chemotherapeutic Docetaxel in the A549 (KRAS G12S) human lung tumor xenograft model. The experimental data determined potential additive or synergistic effects of Plinabulin in combination with Docetaxel in the A549 model.

A549 Human Lung Tumor Xenograft Model

Female nude mice (nu/nu) between 5 and 6 weeks of age weighing approximately 20 g were obtained from Harlan, Inc. (Madison, Wis.). The A549 human lung tumor cell line was obtained from the American Type Culture Collection (ATCC). The A549 human lung tumor cell line had mutation at KRAS G12S. The tumor originates from an explant culture of lung carcinomatous tissue from a 58 yr old caucasian male. Animals were implanted subcutaneously (s.c.) by trocar with fragments of A549 human tumor carcinomas harvested from s.c. growing tumors in nude mice hosts. When the tumors were approximately 46 mg in size (18 days following inoculation), the animals were pair-matched into treatment and control groups. The negative control group contained 8 tumor mice and all other groups contained 9 tumor mice. Each mouse was ear-tagged and followed individually throughout the experiment. The study was conducted in a non-GLP setting. Initial doses were given on Day 1 following pair matching. Plinabulin at 7.5 mg/kg was administered i.p. on two different schedules—Days 1, 4, 8, 11, and 15 and qdx5 (once dose every day for five days). 12.5% dimethylsulfoxide (DMSO), 5% cremophor, and 82.5% peanut oil were combined and administered i.p.; qdx5 to serve as the negative control. Docetaxel (Aventis) was administered i.v. on Days 1, 3, and 5 at 12.5 mg/kg was administered i.p.; wklyx3 at 100 mg/kg to serve as the positive control. Plinabulin at 7.5 mg/kg with the qdx5 schedule was also administered in combination with Docetaxel at the same dose, route, and schedule as the single agent. In the Plinabulin and Docetaxel combination group, Docetaxel was administered 15-30 minutes prior to Plinabulin.

Plinabulin was weighed, and then 12.5% DMSO, 5% cremophor, and 82.5% peanut oil was added, respectively. Finally, the compounds were mixed by vortex and injected within one hour.

Each group contained eight mice. Mice were weighed twice weekly, and tumor measurements were obtained using calipers twice weekly, starting on Day 1. These tumor measurements were converted to mg tumor weight by the standard formula, (W2×L)/2. The experiment was terminated when the control group tumor size reached an average of 1 gram. Upon termination, the mice were weighed, sacrificed and their tumors were excised. The tumors were weighed, and the mean tumor weight per group was calculated. In this model, the mean treated tumor weight/mean control tumor weight×100 was subtracted from 100% to give the tumor growth inhibition (TGI) for each group. One-tailed t-tests using GraphPad Prism© Software (Macintosh version 3.0) were used to calculate p-values.

Some agents may have caused tumor shrinkage in this tumor xenograft model. With these agents, the final weight of a given tumor was subtracted from its own weight at the start of treatment on Day 1. This difference was divided by the initial tumor weight to give the % regression. A mean % tumor regression was calculated from data from mice in a group that experienced tumor regressions.

Negative and Positive Controls

The negative control group had a final mean tumor weight on Day 56 of 870.4 mg±305.1. Docetaxel (12.5 mg/kg; i.v.; Days 1, 3, 5) served as the positive control for the study and had a final mean tumor weight of 655.1 mg±109.2 and 691.4±175.8, respectively. This resulted in a TGI of 26.1% for Docetaxel, compared to the vehicle control group and was within the expected activity range seen in past A549 studies performed. There were no toxic deaths observed in the Docetaxel or Irinotecan groups.

Animals in the Docetaxel group experienced some weight loss. On Day 11, initial mean weight loss was recorded at 2.7%. By Day 22, animals had regained their weight and showed a positive weight gain of 15.4%. There were no toxic deaths observed in the positive control group.

Plinabulin and Docetaxel Combination

Intraperitoneal administration of Plinabulin at 7.5 mg/kg on Days 1-5 resulted in a mean final tumor weight of 1525.7 mg±355.3. The combination group of Plinabulin (7.5 mg/kg; Days 1-5) and Docetaxel (12.5 mg/kg; i.v.; Days 1,3,5) had a final mean tumor weight on Day 56 of 265.8 mg±113.1. This resulted in a TGI of 74.3%. The combination was superior to the Docetaxel treatment group, which had a mean final tumor weight of 655.1 mg±109, and the difference between the combination group and the Docetaxel single agent group was statistically significant (p<0.05).

Animals in the Plinabulin single agent group experienced weight gain. On Days 11 and 22, mean weight gain was recorded at 10.6% and 21.8%, respectively. There were no toxic deaths observed in this dose group. Animals in the combination group experienced weight loss. On Day 11, initial mean weight loss was recorded at 2.7%. By Day 22, animals had regained their weight and showed a 16% weight gain.

Figure 3:
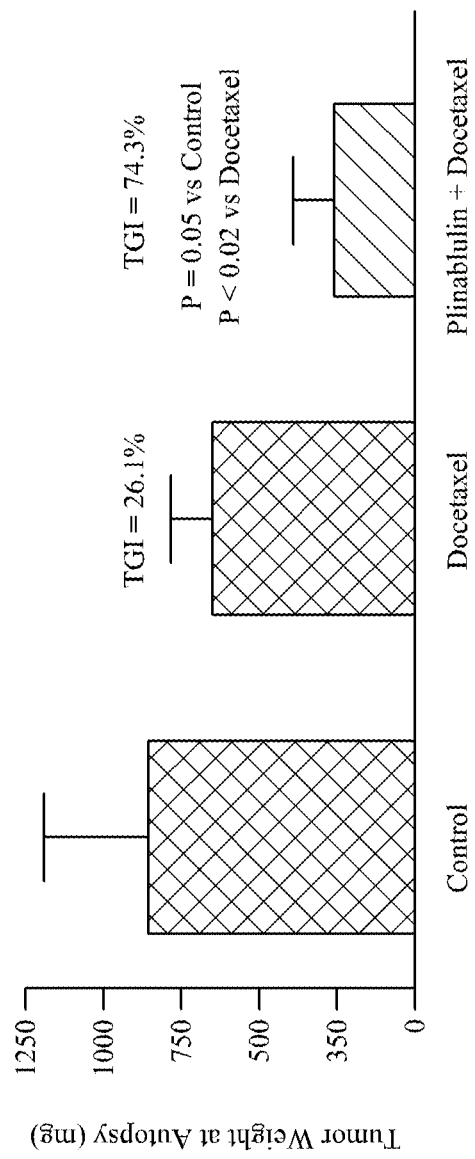
FIG. 3 shows the tumor weight autopsy in mice treated with vehicle only, Docetaxel only, and a combination of Plinabulin and Docetaxel.

At the dose levels and schedules evaluated, animals experienced no toxicity with Plinabulin as a single agent. In all five studies, only one death occurred in the Plinabulin group when administered as a single agent. FIG. 3 shows the tumor weight autopsy in the mice when Plinabulin (7.5 mg/kg) was used in combination with Docetaxel (12.5 mg/kg) through intraperitoneal route. Plinabulin in combination with Docetaxel against the A549 lung tumor model demonstrated a statistically significant (p<0.05) increase in TGI, when compared to Docetaxel alone (74.3% vs. 26.1%). The results indicated strong tumor growth inhibition for the combination of Plinabulin and Docetaxel when compared to Docetaxel as a single agent, showing potential additive or synergistic effects of Plinabulin in combination with Docetaxel in the A549 (KRAS G12S) human lung tumor xenograft model.

Example 3

The mouse model of glioma used was a PDGF-driven GEMM of glioma that mimics the proneural molecular subgroup of glioblastoma (GBM). This model was based on somatic cell-specific gene transfer; the replication-competent ALV-splice acceptor (RCAS) retroviral system allowed the instillation of particular genetic alterations within tightly regulated windows of differentiation in a cell type-specific manner. The RCAS/tv-α system employed the RCAS retroviral vector to infect mice genetically engineered to express the RCAS receptor (tv-α) in specific cell populations. Here, gliomas were generated by RCAS-mediated transfer of PDGF to nestin-expressing cells in the brain. Nestin was expressed in a stem/progenitor cell population in the brain, and has been demonstrated to be a marker for cancer stem cells located in perivascular regions (PVN) in both human and mouse brain tumors. PDGF-driven gliomas arose with complete penetrance when combined with Ink4a-arf-/- deletion by 4-5 weeks post-infection. These tumors closely mimicked the "proneural" subtype of GBM, in which CDKN2A (encoding for both p16INK4A and p14ARF) deletion was observed in 56% of "proneural" human gliomas. The tumor cell structures that define human gliomas, such as Scherer structures, microvascular proliferation and pseudopalisading necrosis were recreated in this GEMM as shown in FIGS. 1a-1d. Moreover, glioma cells migrated along white matter tracks, surrounded neurons and blood vessels and accumulate at the edge of the brain in the sub-pial space. In this regard, PDGF-driven GEMMs of glioma closely resembles PN-GBM, and represents an excellent experimental system to define the interactions between tumor cells and non-neoplastic cells in the tumor microenvironment.

Figure 2:
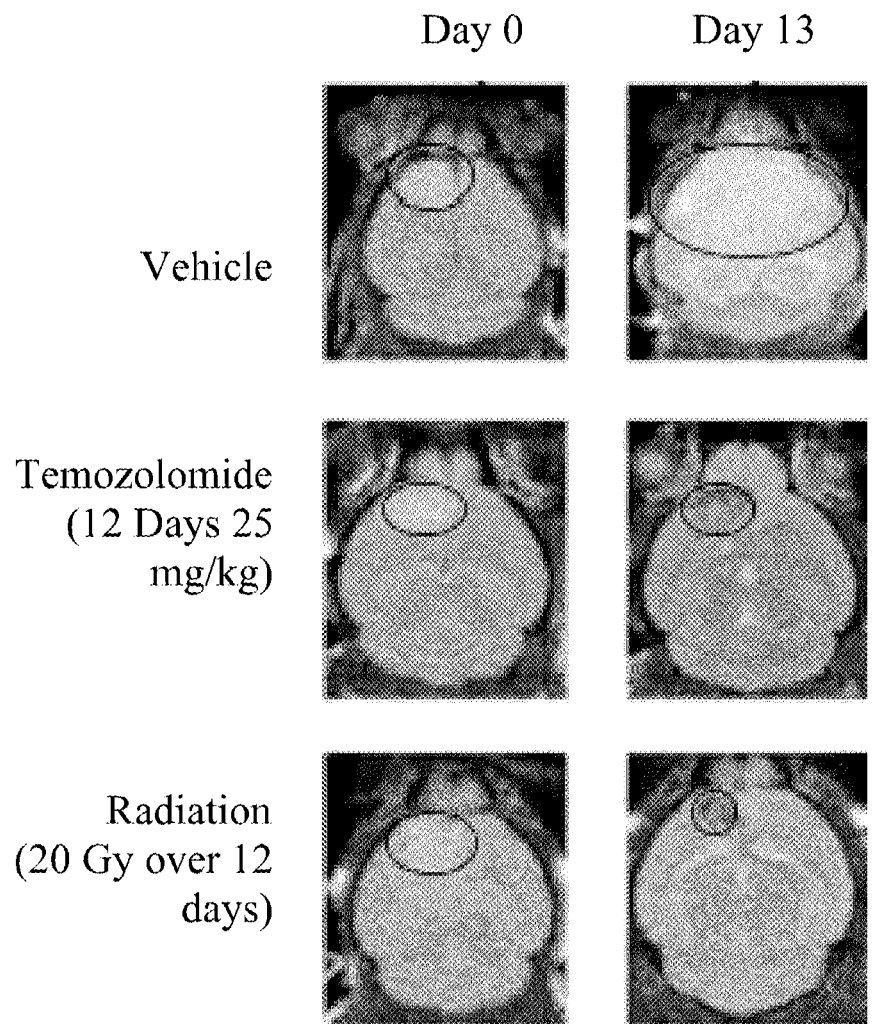
FIG. 2 shows tumor size of mice with PDGF-induced gliomas treated with vehicle, temozolomide or fractionated radiation.

The PDGF-induced model of glioma were used to determine response to radiation and temozolomide as shown in FIG. 2. Glioma-bearing mice were identified by symptoms and verified by T2 weighted MRI. These mice were either treated with vehicle, temozolomide at 25 mg/kg daily for 12 days, or fractionated radiation at a dose of 2 Gy per day 5 days per week for 2 weeks (20 Gy total). The top two images in FIG. 2 shows the growth of tumors that were untreated (vehicle); and in contrast, both the temozolomide treated and irradiated tumors shrank in volume over that same period of time. These tumors recurred after treatment and all animals died of recurrent tumor as can be seen in the survival curves for these corresponding cohorts of mice. The testing data for treatment with radiation and temozolomide illustrated that: 1) trials were performed in this mouse model, 2) the effect of these treatments on mice survival mirrored the human condition, 3) all the mice died of disease, and 4) the relatively homogenous outcomes of these murine cohorts supported the use of this experimental paradigm to detect survival differences in the study.

PDGF-induced model of glioma prepared using the procedures described above were generated. The mice were transgenic for expression of the RCAS receptor (tv-α) from the nestin promoter and having a background of ink4a/arf-/- and lox-stop-lox luciferase, were infected with RCAS-PDGF and RCAS-KRAS that expressed G12D mutant KRAS. The resultant tumors occurred within the first 3-4 weeks. The tumors had the histological characteristics of GBM and can be identified by symptoms of lethargy and poor grooming, MRI scans using a T2 weighted sequence, or bioluminescence imaging with an IVIS system. Mice in the treatment group (KRAS tumor) were administered i.p. with Plinabulin 7.5 mg/kg two times per week for 10 wks, and mice in the control group were administered with Plinabulin diluent (40% wt Kolliphor® HS15 and 60% wt propylene glycol) only. These treated mice began to gain weight and show improved symptoms within a few days Plinabulin was tested on Mice with PDGF-induced gliomas that expressed G12D mutant KRAS. 4-6 week old nestin-tv-α/ink4a-arf-/- mice were anesthetized with Isoflurane and injected with Df-1 cells transfected RCAS-PDGF-B-HA, RCAS-KRAS. Mice were injected with one microliter of a 1:1 mixture of $2 \times 10^5$ RCAS-PDGF-B-HA/RCAS-KRAS using a stereotactic frame via a 26-gauge needle attached to a Hamilton syringe. Cells were injected into the right frontal cortex, coordinates bregma 1.75 mm, Lat −0.5 mm, and a depth of 2 mm. Mice were monitored carefully for weight loss and put on the study when they lost >0.3 grams total over 2 consecutive days or displayed outward signs of a tumor. The mice were entered into a study group and treated with either Plinabulin or Plinabulin diluent as described above while consecutively being monitored for lethargy, hunched posture, appetite loss, outward signs of tumor growth, agitation, weight-loss and overall failure to thrive. The mice were sacrificed when they lost more than 20% of their body weight, mobility, inability to feed or weighed less than 14 grams for a male/12 grams for a female. The mice were sacrificed using $CO_2$, brains were harvested and stored O/N in 10% Neutral buffered formalin and then replaced with Flex 80 and stored at 4 degrees.

Figure 4:
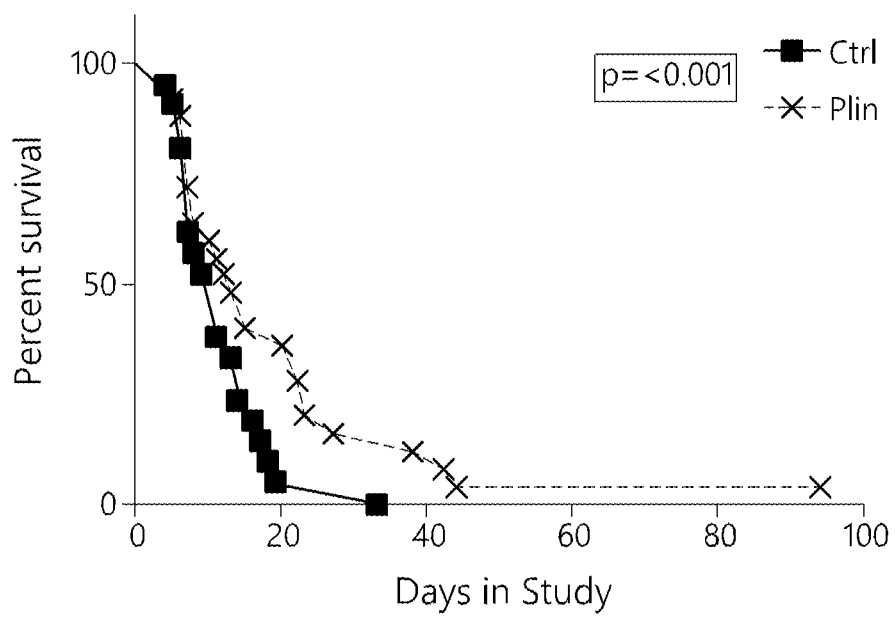
FIG. 4 shows the survival rate of mice with PDGF-induced gliomas characterized by expression of KRAS mutation that were treated with control and Plinabulin.

FIG. 4 shows the survival rate of mice with Glioblastoma with the G12D Kras mutation. As shown in FIG. 4, mice having the PDGF-induced model of Glioblastoma generally had a significantly better survival rate in the Plinabulin treated group as compared to the control group (p=0.001).

Example 4

Mice with PDGF-induced gliomas that expressed G12D mutant KRAS were prepared using the procedures according to Example 3 and used in this experiment. 4-6 week old nestin-tv-α/ink4a-arf-/- mice were anesthetized with Isoflurane and injected with Df-1 cells transfected RCAS-PDGF-B-HA, RCAS-KRAS. Mice were injected with one microliter of a 1:1 mixture of $2 \times 10^5$ RCAS-PDGF-B-HA/RCAS-KRAS using a stereotactic frame via a 26-gauge needle attached to a Hamilton syringe. Cells were injected into the right frontal cortex, coordinates bregma 1.75 mm, Lat -0.5 mm, and a depth of 2 mm. Mice were monitored carefully for weight loss and put on the study when they lost >0.3 grams total over 2 consecutive days or displayed outward signs of a tumor.

Figure 5:
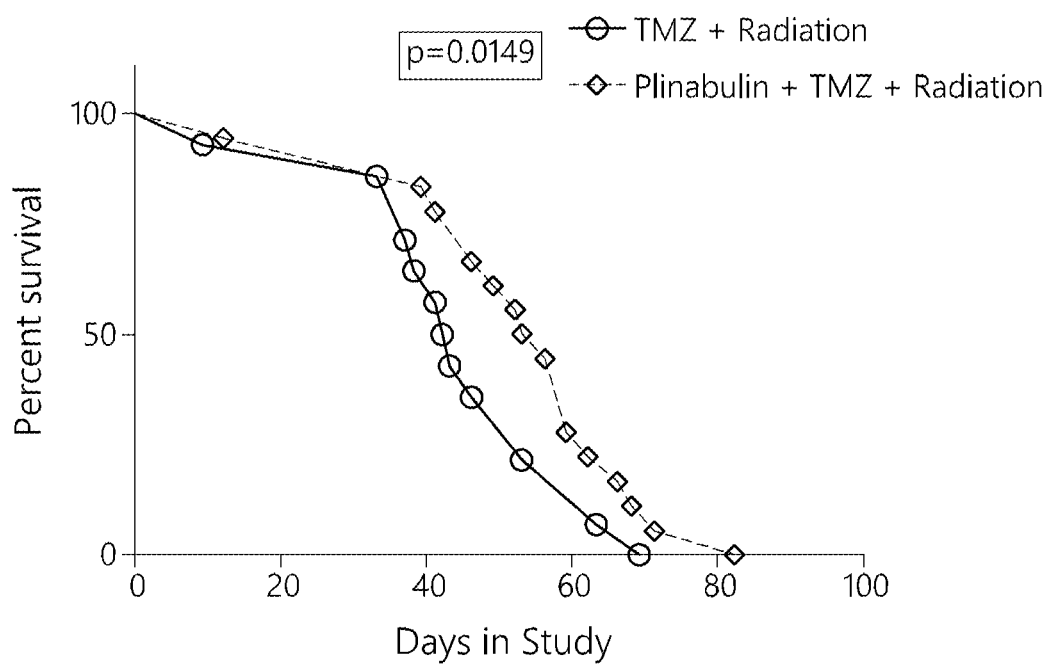
FIG. 5 shows the survival rate of mice with PDGF-induced gliomas characterized by expression of KRAS mutation that were treated with the combination of plinabulin, temozolomide, and radiation and the combination of temozolomide and radiation.

The mice were entered into two study groups. One group was treated with the combination of temozolomide (TMZ), Radiation and Plinabulin: radiation was given at 10 gy x1, TMZ and Plinabulin 7.5 mg/kg in Plinabulin diluent was administered intraperitoneally twice a week on Monday and Thursday for 10 weeks. The other group, the control group, was treated with the combination of TMZ and radiation: radiation was given at 10 gy x1, TMZ was administered intraperitoneally twice a week on Monday and Thursday for 10 weeks. The mice were monitored for lethargy, hunched posture, appetite loss, outward signs of tumor growth, agitation, weight-loss and overall failure to thrive. The mice were sacrificed when they lost more than 20% of their body weight, mobility, inability to feed or weighed less than 14 grams for a male/12 grams for a female. The mice were sacrificed using $CO_2$, brains were harvested and stored O/N in 10% Neutral buffered formalin and then replaced with Flex 80 and stored at 4 degrees. As shown in FIG. 5, the mice having the PDGF-induced model of Glioblastoma generally had significantly better survival rate in the Plinabulin, TMZ, and radiation treated group as compared to the control group that received TMZ and radiation (p=0.0149).

Example 5

The combination of Plinabulin and irinotecan was tested and its activity was compared to the standard chemotherapeutic irinotecan in the HCT-15 (KRAS mutation G13D; P53 mutation S241F) human colon tumor xenograft model. The experimental data determined synergistic effects of Plinabulin in combination with irinotecan in the HCT-15 model.

HCT-15 Human Colon Tumor Xenograft Model

Female Athymic nude mice (Hsd:Athymic Nude-Foxn1$_{nu}$) were supplied by Harlan (Indianapolis, Ind.). Mice were received at 4 weeks of age. All mice were acclimated prior to handling. The HCT-15 human colon tumor cell line was received from ATCC (Manassas, Va.). Cultures were maintained in RPMI-1640 (Lonza; Walkersville, Md.) supplemented with 10% fetal bovine serum (FBS; Seradigm; Radnor, Pa.), and housed in a 5% CO2 atmosphere. The cultures were expanded in tissue culture flasks at a 1:10 split ratio until a sufficient amount of cells were harvested. The HCT-15 human colon tumor cell line had mutations at KRAS G13D and P53 S241F.

Female mice were inoculated in the subcutaneous right flank with 0.1 ml of a 50% Media/50% Matrigel mixture containing a suspension of HCT-15 tumor cells ($5 \times 10_6$ cells/mouse).

Plinabulin (80 mg/20 mL in 40% Solutol:60% propylene glycol) was diluted in a sterile 5% dextrose solution to a concentration of 0.75 mg/mL. Plinabulin at 7.5 mg/kg was administered i.p. twice weekly until the end of the study. Plinabulin vehicle (40% soltol:60% propylene glycol) was diluted in sterile 5% dextrose solution in the same ratio as for plinabulin and was used as a negative control. Irinotecan (Teva Pharmaceuticals (Irvine, Calif.) was diluted in 0.9% sodium chloride solution to a concentration of 10 mg/ml to deliver a dose of 100 mg/kg in a 10 ml/kg dose volume. Irinotecan was dosed intraperitoneally at a dose of 100 mg/kg once weekly for three weeks to serve as a positive control. Plinabulin was also administered in combination with irinotecan at the same dose, route, and schedule as the single agent. In the Plinabulin and irinotecan combination group, irinotecan was administered 120 minutes prior to Plinabulin Seven days following inoculation, tumors were measured using a digital caliper. The calipers were used to measure width and length diameters of the tumor. The measured values were digitally recorded using animal study management software, Study Director V.2.1.1 (Study Log). Tumor volumes were calculated utilizing the formula: Tumor volume (mm3)=(a×b$_2$/2) where 'b' is the smallest diameter and 'a' is the largest diameter$_1$. Forty mice with tumor sizes of 104-125 mm$_3$ were randomized into four groups of ten mice, each with a mean of approximately 112 mm$_3$, by random equilibration using Study Director (Day 1). Tumor volumes and body weights were recorded when the mice were randomized and were taken twice weekly thereafter. Clinical observations were made daily.

The experiment was terminated when the control group tumor size reached an average of 1 gram. Upon termination, the mice were weighed, sacrificed and their tumors were excised. The tumors were weighed, and the mean tumor weight per group was calculated as well as a visual assessment of tumor necrosis.

Mean tumor growth inhibition (TGI) was calculated for Day 27 (the final day of the study). All statistical analyses in the xenograft study were performed with Prism GraphPad® v6.00 software. Differences in Day 27 tumor volumes were confirmed using the Analysis of Variance (ANOVA) test.

Negative and Positive Controls

The negative control group had a final mean tumor volume on Day 27 of 1701.4 mm$^3$±178.0. Irinotecan (100 mg/kg; i.p.; Days 1, 8, 15) served as the positive control for the study and had a final mean tumor volume of 1196.2 mm$^3$±121.7. This resulted in a TGI of 31.8% for irinotecan, compared to the vehicle negative control group. There were no toxic deaths observed in the negative control or positive groups.

Treatment with vehicle negative control, Plinabulin, and irinotecan were well-tolerated. Some mild body weight loss occurred with the vehicle control group and Plinabulin group in the final few days of the study, but body weight loss was not substantial. Clinical observations consisted primarily of tumor necrosis, which is typical for this tumor model. Combination treatment with Plinabulin and irinotecan was fairly well-tolerated with moderate body weight loss observed.

The combination group of Plinabulin (7.5 mg/kg; Days 1-5) and irinotecan (100 mg/kg, days 1,8 and 15) had a final mean tumor volume on Day 27 of 766.8 mm$^3$±84.2. This resulted in a TGI of 58.8%. The combination was superior to the irinotecan treatment group, which had a mean final tumor volume of 1196.2 mm$^3$±121.7, and the difference between the combination group and the irinotecan single agent group was statistically significant (p<0.05).

Figure 6:
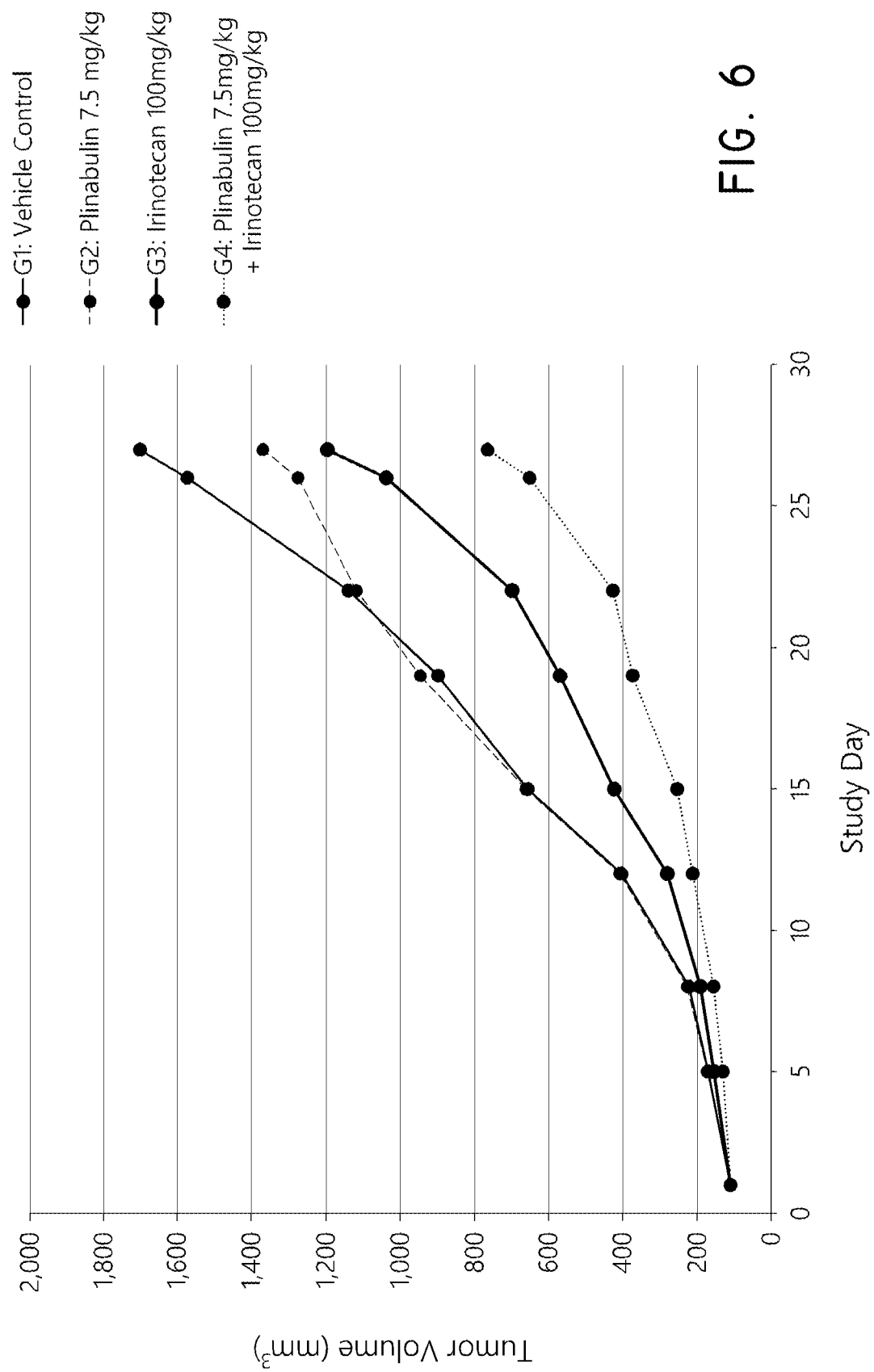
FIG. 6 shows the change in tumor volume in mice with the HCT-15 (Kras mutation G13D) human colon tumor xenograft throughout the course of the study in mice treated with vehicle control, plinabulin, irinotecan, or the combination of plinabulin and irinotecan.

At the dose levels and schedules evaluated, animals experienced no toxicity with Plinabulin as a single agent. FIG. 6 shows the tumor volume over the course of the study in the mice when Plinabulin (7.5 mg/kg) was used in combination with irinotecan (100 mg/kg) via the intraperitoneal route. Plinabulin in combination with irinotecan against the HCT-15 colon tumor model demonstrated a statistically significant (p<0.05) increase in TGI, when compared to irinotecan alone (58.8% vs. 31.8%). The results indicated strong tumor growth inhibition for the combination of Plinabulin and irinotecan when compared to irinotecan as a single agent, showing potential additive or synergistic effect of Plinabulin in combination with irinotecan in the HCT-15 (KRAS G13D) human colon tumor xenograft model.

Example 6

The combination of Plinabulin and irinotecan was tested and its activity was compared to irinotecan alone in the LoVo (KRAS mutation p.G13D) human colon tumor xenograft model. The experimental data determined potential additive or synergistic effects of Plinabulin in combination with irinotecan in the LoVo model.

LoVo Human Colon Tumor Xenograft Model: Female Athymic nude mice (Hsd:Athymic Nude-Foxn1$_{nu}$) were supplied by Harlan (Indianapolis, Ind.). Mice were received at 4 weeks of age. All mice were acclimated prior to handling. The LoVo human colon tumor cell line was received from ATCC (Manassas, Va.). Cultures were maintained in F12-K (Corning/Cellgro, Manassas, Va.) supplemented with 10% fetal bovine serum (FBS; Seradigm; Radnor, Pa.), and housed in a 5% CO$_2$ atmosphere. The cultures were expanded in tissue culture flasks at a 1:3 split ratio until a sufficient amount of cells were harvested. The LoVo human colon tumor cell line had mutations at KRAS p.G13D.

Female mice were inoculated in the subcutaneous right flank with 0.1 ml of a 50% Media/50% Matrigel mixture containing a suspension of LoVo tumor cells (1×10$^7$ cells/mouse).

Plinabulin (80 mg/20 mL in 40% Solutol:60% propylene glycol) was diluted in a sterile 5% dextrose solution to a concentration of 0.75 mg/mL. Plinabulin at 7.5 mg/kg was administered i.p. twice weekly until the end of the study. Plinabulin vehicle (40% soltol:60% propylene glycol) was diluted in sterile 5% dextrose solution in the same ratio as for plinabulin and was used as a negative control. Irinotecan (Teva Pharmaceuticals (Irvine, Calif.) was diluted in 0.9% sodium chloride solution to a concentration of 10 mg/ml to deliver a dose of 100 mg/kg in a 10 ml/kg dose volume. Irinotecan was dosed intraperitoneally at a dose of 80 mg/kg once weekly for three weeks to serve as the positive control. Plinabulin was also administered in combination with irinotecan at the same dose, route, and schedule as each of the single agents. In the Plinabulin and Irinotecan combination group, Irinotecan was administered 120 minutes prior to Plinabulin.

Seven days following inoculation, tumors were measured using a digital caliper. The calipers were used to measure width and length diameters of the tumor. The measured values were digitally recorded using animal study management software, Study Director V.2.1.1 (Study Log). Tumor volumes were calculated utilizing the formula: Tumor volume (mm$_3$)=(a×b$_2$/2) where 'b' is the smallest diameter and 'a' is the largest diameter$_1$. Forty mice with tumor sizes of 104-125 mm$_3$ were randomized into four groups of ten mice, each with a mean of approximately 112 mm$_3$, by random equilibration using Study Director (Day 1). Tumor volumes and body weights were recorded when the mice were randomized and were taken twice weekly thereafter. Clinical observations were made daily.

The vehicle control was sacrificed after reaching a mean tumor volume of equal to or greater than 1500 mm$_3$ on Day 15 as outlined in the protocol. The treatment groups were ended when the irinotecan group reached a mean tumor volume of 774 mm$_3$ due to mice being found dead or moribund sacrificed. At time of necropsy, the tumors were excised and wet weight measurements were recorded as well as a visual assessment of tumor necrosis.

Mean tumor growth inhibition (TGI) was calculated for Day 27. All statistical analyses in the xenograft study were performed with Prism GraphPad® v6.00 software. Differences in Day 27 tumor volumes were confirmed using the Analysis of Variance (ANOVA) test. A one-tailed Student's T-Test with Welch's correction was also used to verify any differences between each group and the vehicle control, and a two-tailed Student's T-Test was used to verify differences between combination groups and their respective single agents.

The Vehicle Control reached a mean tumor volume of 2078.1 mm$^3$ on Day 15. This group experienced no appreciable mean body weight loss throughout the study. Nine of ten mice experienced slight to moderate tumor necrosis first observed on Day 12. All animals survived to terminal sacrifice.

Treatment with Plinabulin 7.5 mg/kg resulted in a mean tumor volume of 1279.2 mm$^3$ on Day 15. This group produced a TGI of 41.0% (n=7) on Day 15. A significant decrease in mean tumor volume was observed (p<0.05) when compared to the vehicle control on Day 15(Student's T-test). This group experienced no mean body weight loss throughout the study. Nine of ten mice experienced slight to severe tumor necrosis first observed on Day 12. Mouse 5 was moribund sacrificed on Day 19 due to clinical observations indicating morbidity from severe tumor necrosis. Mouse 2, 3, 4, 7, and 10 were found dead during the study. Mouse 8 was found dead due to technical error. Three out of ten mice survived to terminal sacrifice.

Treatment with irinotecan 80 mg/kg resulted in a mean tumor volume of 1156.7 mm$^3$ on Day 15. This group produced a TGI of 47.2% (n=10) when compared to the vehicle control on Day 15. A significant decrease in mean tumor volume was observed (p<0.05) when compared to the vehicle control on Day 15 (Student's T-test). This group experienced moderate body weight loss with a maximum of 7.4% on Day 20, the final day of the study. Eight of ten mice experienced slight to severe tumor necrosis first observed on Day 12. Mouse 3, 4, and 5 were moribund sacrificed on Day 19, 15, and 18 respectively due to clinical observations indicating morbidity from severe tumor necrosis. Mouse 1 and 10 were found dead on Day 17 and 20 respectively. Five out of ten mice survived to terminal sacrifice.

Figure 7:
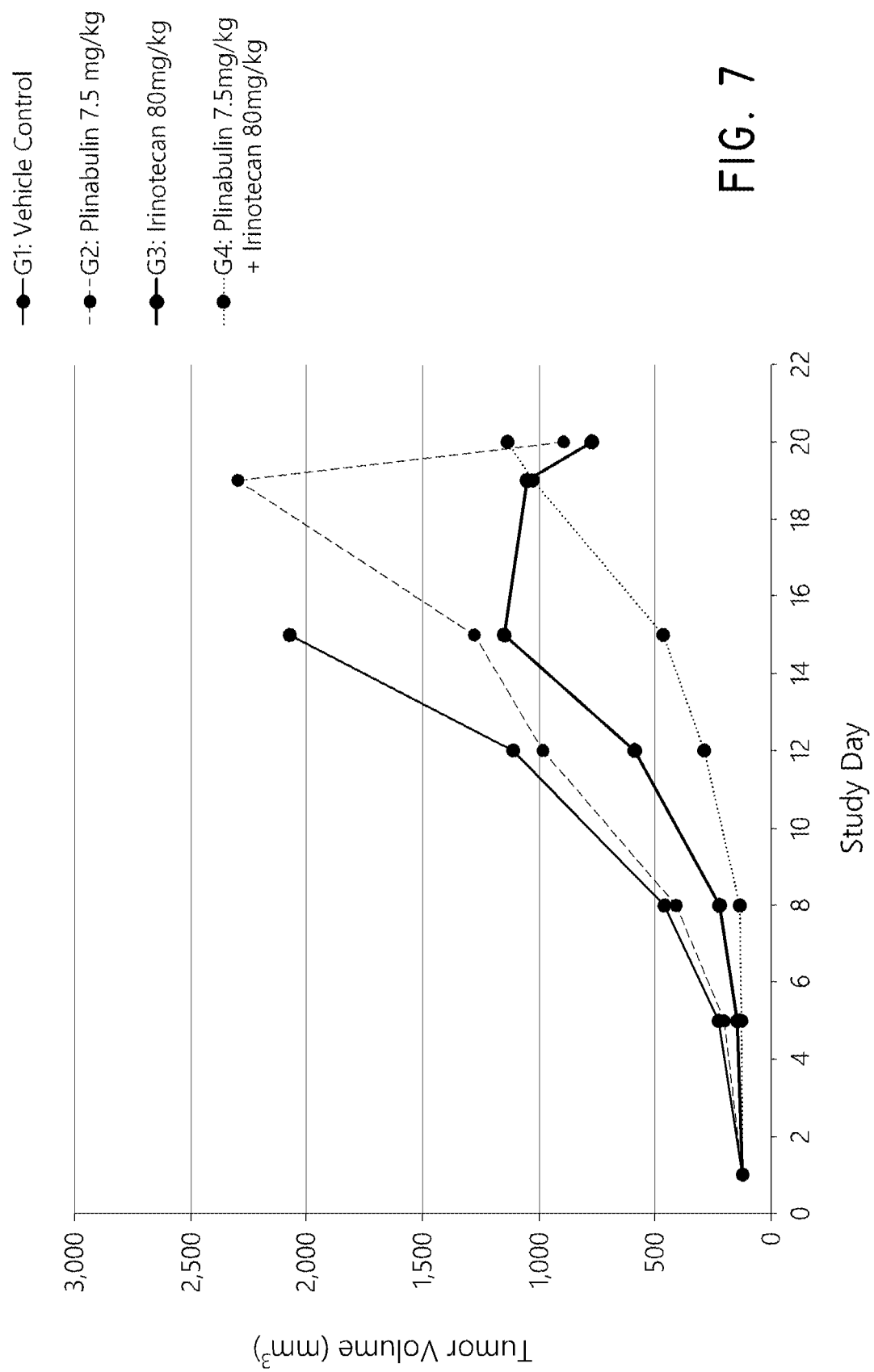
FIG. 7 shows the change in tumor volume in mice with the Lovo (Kras mutation, p.G13D) human colon tumor xenograft throughout the course of the study in mice treated with vehicle control, plinabulin, irinotecan, or the combination of plinabulin and irinotecan.

Treatment with Plinabulin 7.5 mg/kg and irinotecan 80 mg/kg resulted in a mean tumor volume of 468.4 mm$_3$ by Day 15. This group produced a TGI of 82.4% (n=10) when compared to the vehicle control on Day 15. A significant decrease in mean tumor volume was observed (p<0.05) when compared to the vehicle control on Day 15 (Student's T-test) and single agent Plinabulin (Student's T-test). No significant difference in mean tumor volume was observed when compared to single agent irinotecan on Day 15. This group experienced moderate body weight loss with a maximum of 5.8% on Day 20, the final day of the study. Five of ten mice experienced slight to moderate tumor necrosis first observed on Day 15. All ten mice survived to terminal sacrifice. As shown in FIG. 7, the combination of Plinabulin and irinotecan outperformed irinotecan as a single agent. Due to the loss of mice in the irinotecan alone group, the mean tumor volumes decreased from 1157 mm$^3$ on Day 15 to 774 mm$^3$ on Day 20, causing the perceived shift in performance.

What is claimed is:

1. A method of therapeutically treating a cancer characterized by expressing a mutant form of a RAS protein, comprising administering Plinabulin to a subject in need thereof, wherein:
   the mutant form of the RAS protein is a mutant form of a NRAS protein, a mutant form of an HRAS protein, or a mutant form of a KRAS protein that comprises one or more amino acid substitutions selected from the group consisting of G12C, G12R, G12D, G12F, G12L, G12N, G13C, G13R, G13S, G13A, G13V, G13P, S17G, P34S, A59E, A59G, A59T, Q61K, Q61R, Q61H, K117N, A146P, A146T, A146V, and D153V.

2. The method of claim 1, wherein the cancer is selected from colorectal cancer, pancreatic cancer, renal caner, lung cancer, liver cancer, breast cancer, prostate cancer, gastrointestinal cancer, peritoneal cancer, melanoma, endometrial cancer, ovarian cancer, cervical cancer, uterine carcinoma, bladder cancer, glioblastoma, brain metastases, salivary gland carcinoma, thyroid cancer, brain cancer, lymphoma, myeloma, and head and neck cancer.

3. The method of claim 1, wherein the cancer is selected from squamous cell cancer, small-cell lung cancer, non-small cell lung cancer, adenocarcinoma of the lung, squamous carcinoma of the lung, hepatocellular carcinoma, colon cancer, endometrial carcinoma, and hepatocellular carcinoma.

4. The method of claim 1, comprising co-administering Plinabulin with an additional therapeutic agent selected from temozolomide, bevicizumab, everolimus, carmustine, lomustine, procarbazine, vincristine, irinotecan, cisplatin, carboplatin, methatrexate, etoposide, vinblasatine, bleomycin, actinomycin, cyclophosphamide, or ifosfamide.

5. The method of claim 1, wherein the Plinabulin is administered at a dose from about 5 mg/m$^2$ to 150 mg/m$^2$.

6. The method of claim 1, wherein the Plinabulin is administered orally, sublingually, buccally, subcutaneously, intravenously, intranasally, topically, transdermally, intradermally, intraperitoneally, intramuscularly, intrapulmonarilly, vaginally, rectally, or intraocularly.

7. The method of claim 1, wherein the Plinabulin is administered in combination with radiation.

8. The method of claim 1, wherein the Plinabulin is administered once a week.

9. The method of claim 1, wherein the Plinabulin is administered once on each of day 1 and day 8 of a three-week (21 day) treatment cycle.

10. A method of inhibiting proliferation of a cell having a RAS mutation, comprising contacting the cell with Plinabulin, wherein:
    the mutant form of the RAS protein is a mutant form of a NRAS protein, a mutant form of an HRAS protein, or a mutant form of a KRAS protein that comprises one or more amino acid substitutions selected from the group consisting of G12C, G12R, G12D, G12F, G12L, G12N, G13C, G13R, G13S, G13A, G13V, G13P, S17G, P34S, A59E, A59G, A59T, Q61K, Q61R, Q61H, K117N, A146P, A146T, A146V, and D153V.

11. The method of claim 10, wherein the contacting comprises administering Plinabulin to a subject having the cell.

12. The method of claim 10, wherein the mutant form of the RAS protein is a KRAS protein that comprises one or more amino acid substitutions selected from the group consisting of G12C, G12R, G12F, G12L, G12N, G12D, G13C, G13S, G13V, G13P, S17G, P34S, A59E, A59G, A59T, Q61K, Q61R, and Q61H.

13. The method of claim 10, wherein the Plinabulin is administered at a dose from about 5 mg/m$^2$ to 150 mg/m$^2$.

14. A method of inducing apoptosis in a cell having a RAS mutation, comprising contacting the cell with Plinabulin, wherein:
    the mutant form of the RAS protein is a mutant form of a NRAS protein, a mutant form of an HRAS protein, or a mutant form of a KRAS protein that comprises one or more amino acid substitutions selected from the group consisting of G12C, G12R, G12D, G12F, G12L, G12N, G13C, G13R, G13S, G13A, G13V, G13P, S17G, P34S, A59E, A59G, A59T, Q61K, Q61R, Q61H, K117N, A146P, A146T, A146V, and D153V.

15. The method of claim 14, wherein the mutant form of the RAS protein is a KRAS protein that comprises one or more amino acid substitutions selected from the group consisting of G12C, G12R, G12F, G12L, G12N, G12D, G13C, G13S, G13V, G13P, S17G, P34S, A59E, A59G, A59T, Q61K, Q61R, and Q61H.

16. The method of claim 14, wherein the Plinabulin is administered at a dose from about 5 mg/m$^2$ to 150 mg/m$^2$.

17. A method of inhibiting progression of a cancer characterized by expressing a mutant form of a RAS protein in a subject, comprising administering Plinabulin to a subject in need thereof, wherein
    the mutant form of the RAS protein is a mutant form of a NRAS protein, a mutant form of an HRAS protein, or a mutant form of a KRAS protein that comprises one or more amino acid substitutions selected from the group consisting of G12C, G12R, G12D, G12F, G12L, G12N, G13C, G13R, G13S, G13A, G13V, G13P, S17G, P34S, A59E, A59G, A59T, Q61K, Q61R, Q61H, K117N, A146P, A146T, A146V, and D153V.

18. The method of claim 17, wherein the mutant form of the RAS protein is a KRAS protein that comprises one or more amino acid substitutions selected from the group consisting of G12C, G12R, G12F, G12L, G12N, G12D, G13C, G13S, G13V, G13P, S17G, P34S, A59E, A59G, A59T, Q61K, Q61R, and Q61H.

19. The method of claim 17, wherein the Plinabulin is administered at a dose from about 5 mg/m$^2$ to 150 mg/m$^2$.

20. The method of claim 17, wherein the Plinabulin is administered once on each of day 1 and day 8 of a three-week (21 day) treatment cycle.

* * * * *